(12) United States Patent
Schiano et al.

(10) Patent No.: US 7,511,500 B2
(45) Date of Patent: Mar. 31, 2009

(54) DETECTING QUADRUPOLE RESONANCE SIGNALS USING HIGH TEMPERATURE SUPERCONDUCTING RESONATORS

(75) Inventors: Jeffrey L. Schiano, State College, PA (US); Daniel Swain, Philadelphia, PA (US); Michael A. Pusateri, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/679,378

(22) Filed: Feb. 27, 2007

(65) Prior Publication Data

US 2008/0001602 A1 Jan. 3, 2008

Related U.S. Application Data

(60) Provisional application No. 60/777,461, filed on Feb. 27, 2006, provisional application No. 60/870,876, filed on Dec. 20, 2006, provisional application No. 60/777,476, filed on Feb. 27, 2006, provisional application No. 60/782,654, filed on Mar. 15, 2006.

(51) Int. Cl.
*G01V 3/00* (2006.01)

(52) U.S. Cl. .................................... 324/318

(58) Field of Classification Search ......... 324/300–322; 600/410–435; 333/219–235; 343/741, 787–788, 343/907

See application file for complete search history.

(56) References Cited

U.S. PATENT DOCUMENTS

| | | | |
|---|---|---|---|
| 5,254,950 A | 10/1993 | Fan et al. | |
| 5,351,007 A | 9/1994 | Withers et al. | |
| 5,585,723 A | 12/1996 | Withers | |
| 5,814,992 A | 9/1998 | Busse-Grawitz et al. | |
| 6,100,688 A | 8/2000 | Smith et al. | |
| 6,344,818 B1 | 2/2002 | Markov et al. | |
| 6,392,408 B1 | 5/2002 | Barrall et al. | |
| 6,518,854 B2* | 2/2003 | Kayano et al. | 333/99 S |
| 6,573,766 B1 | 6/2003 | Humphrey et al. | |
| 6,688,127 B2 | 2/2004 | Laubacher et al. | |
| 6,711,912 B2 | 3/2004 | Laubacher et al. | |
| 6,759,930 B2* | 7/2004 | Kayano et al. | 333/99 S |
| 6,778,042 B2* | 8/2004 | Terashima et al. | 333/205 |
| 6,919,783 B2* | 7/2005 | Dionne et al. | 333/205 |
| 6,937,117 B2* | 8/2005 | Terashima et al. | 333/205 |
| 7,106,058 B2 | 9/2006 | Wilker et al. | |

(Continued)

OTHER PUBLICATIONS

Wilker, C., J.D. McCambridge, D.B. Laubacher, R.L. Alvarez, J.S. Guo, C.F. Carter III, M.A. Pusateri, and J.L. Schiano. "HTS Sensors for NQR Spectroscopy." IEEE Microwave Symposium Digest 2004, vol. 1, pp. 143-146.

(Continued)

*Primary Examiner*—Dixomara Vargas
(74) *Attorney, Agent, or Firm*—Gifford, Krass, Sprinkle, Anderson & Citkowski, P.C.

(57) ABSTRACT

Narrowband quadrupole resonance (QR) probes were developed from thin-film high-temperature superconducting (HTS) resonators. The QR probes are useful in analyte-detection systems, in particular for the detection of nitrogen-containing compounds. Embodiments of the invention provide greater than an order of magnitude improvement in sensitivity and the ability to reject RF interference sources located outside the pass-band of a superconducting QR probe. Methods and apparatus are described for analyte detection and resonance frequency adjustment.

13 Claims, 12 Drawing Sheets

U.S. PATENT DOCUMENTS

| | | | |
|---|---|---|---|
| 7,109,714 | B2 | 9/2006 | Rudakov et al. |
| 7,148,684 | B2 | 12/2006 | Laubacher et al. |
| 7,239,150 | B2 * | 7/2007 | Troxler et al. ............... 324/643 |
| 7,323,955 | B2 * | 1/2008 | Jachowski .................. 333/204 |
| 2002/0190715 | A1 | 12/2002 | Marek |
| 2003/0119677 | A1 | 6/2003 | Qiyan et al. |
| 2004/0245988 | A1 | 12/2004 | Laubacher |
| 2005/0046420 | A1 | 3/2005 | Laubacher et al. |
| 2005/0104593 | A1 | 5/2005 | Laubacher |
| 2005/0122109 | A1 | 6/2005 | Wilker et al. |
| 2005/0140371 | A1 | 6/2005 | Alvarez |
| 2005/0206382 | A1 | 9/2005 | Laubacher et al. |
| 2005/0222504 | A1 | 10/2005 | Otvos et al. |
| 2005/0270028 | A1 | 12/2005 | Alvarez et al. |
| 2006/0009172 | A1 | 1/2006 | Shamsaifar |
| 2006/0012371 | A1 | 1/2006 | Laubacher et al. |
| 2006/0017439 | A1 | 1/2006 | Laubacher et al. |
| 2006/0021437 | A1 | 2/2006 | Kaduchak et al. |
| 2006/0082368 | A1 | 4/2006 | McCambridge |
| 2006/0119357 | A1 | 6/2006 | Alvarez et al. |
| 2008/0036462 | A1 * | 2/2008 | Schiano ..................... 324/318 |

OTHER PUBLICATIONS

Bendall, M.R. "Portable NMR Sample Localization Method Using Inhomogeneous rf Irradiation Coils." Chemical Physics Letters 1983, vol. 99, pp. 310-315.

Garroway, A.N., M.L. Buess, J.B. Miller, B.H. Suits, A.D. Hibbs, G.A. Barrall, R. Matthews, L.J. Burnett. "Remote Sensing by Nuclear Quadrupole Resonance." IEEE Transactions on Geoscience and Remote Sensing 2001, vol. 39, pp. 1108-1118.

Withers, R.S., G.C. Liang, B.F. Cole, and M. Johansson. "Thin-Film HTS Probe Coils for Magnetic-Resonance Imaging." IEEE Transactions on Applied Superconductivity 1993, vol. 3, pp. 2450-2453.

Suits, B.H., A.N. Garroway, and J.B. Miller. "Super-Q Detection of Transient Magnetic Resonance Signals." Journal of Magnetic Resonance 1998, vol. 132, pp. 54-64.

Tan, Y., S.L. Tantum, L.M. Collins. "Cramer-Rao Lower Bound for Estimating Quadrupole Resonance Signals in Non-Gaussian Noise." IEEE Signal Processing Letters 2004, vol. 11, pp. 490-493.

Darrasse, L. and J.C. Ginefri. "Perspectives with cryogenic RF probes in biomedical MRI." Biochimie 2003, vol. 85, pp. 915-937.

Black, R.D., P.B. Roemer, and O.M. Mueller. "Electronics for a High Temperature Superconducting Receiver System for Magnetic Resonance Microimaging." IEEE Transactions on Biomedical Engineering 1994, vol. 41, pp. 195-197.

Black, R.D., P.B. Roemer, A. Mogro-Campero, L.G. Turner, and K.W. Rohling. "High temperature superconducting resonator for use in nuclear magnetic resonance microscopy." Applied Physics Letters 1993, vol. 62, pp. 771-773.

Rudakov, T.N., A.V. Belyakov, and V.T. Mikhaltsevich. "A low-frequency instrument for remote nuclear quadrupole resonance experiments." Measurement Science and Technology 1997, vol. 8, pp. 444-448.

Bendall, M.R., A. Connelly, and J.M. McKendry. "Elimination of Coupling between Cylindrical Transmit Coils and Surface-Receive Coils for in Vivo NMR." Magnetic Resonance in Medicine 1986, vol. 3, pp. 157-163.

* cited by examiner

DETECTING QUADRUPOLE RESONANCE SIGNALS USING HIGH TEMPERATURE SUPERCONDUCTING RESONATORS

REFERENCE TO RELATED APPLICATIONS

This application claims reference to U.S. Provisional Patent Application Nos. 60/777,476, filed Feb. 27, 2006; 60/777,461, filed Feb. 27, 2006; 60/782,654, filed Mar. 15, 2006; and 60/870,876, filed Dec. 20, 2006, the entire contents of which are incorporated herein by reference.

FIELD OF THE INVENTION

The present invention relates to quadrupole resonance (QR), in particular to improved QR detection apparatus using high-temperature superconductor (HTS) probes.

BACKGROUND OF THE INVENTION

Quadrupole resonance (QR) allows noninvasive, short-range detection of analytes containing nitrogen, including many explosives. Unlike other technologies, a QR detection system can discriminate among different types of explosives and distinguish them from benign nitrogen compounds, because the QR response from each nitrogen compound has a distinct spectral signature.

There is a great current need to detect explosives concealed within containers, such as luggage, mail, improvised explosive devices, and minimal metal landmines. At the present time, x-ray detection is the primary technology used at aviation security checkpoints. X-ray detection reveals the presence and shape of objects that absorb energy from the x-ray beam, but cannot distinguish between benign material and explosive devices.

Current QR detection systems are hindered by problems such as inadequate sensitivity, limited operating temperature range, and electrical interference from both internal and external RF sources. The signal-to-ratio (SNR) of a nuclear resonance measurement using QR is proportional to the square-root of the Quality-factor (Q-factor) of the probe. Q-factors are approximately 100 for normal (non superconducting) metal coils, which severely limits the SNR.

The frequency of the QR response from a particular nitrogen compound is temperature dependent, and existing commercial QR detection systems requires that the searched objects be held within small temperature range. Further, the small QR response is easily masked by RF sources, such as AM broadcast stations and engine ignition noise, that are external to the detection system.

Excitation of a QR response requires the application of a pulsed RF magnetic field within the search volume. The applied RF pulse may excite spurious responses from materials within the search volume that can obscure the QR response, leading to an unacceptably large false alarm rate. Examples of internal noise sources include the decaying magnetic field generated by currents induced within conductive materials located within the search volume, as well as piezoelectric responses from materials within the search volume.

SUMMARY OF THE INVENTION

Narrowband quadrupole resonance (QR) probes from thin-film high-temperature superconducting (HTS) resonators are described. The superconducting QR probe can be used in systems that detect explosives concealed within containers such as luggage, mail, improvised explosive devices, and minimal metal landmines. In comparison to existing QR probes fabricated from normal (non-superconducting) probes, a superconducting QR probe improves the signal-to-noise ratio per unit time by more than an order of magnitude. Embodiments of the invention provide greater than an order of magnitude improvement in sensitivity, the ability to reject RF interference sources located outside the pass-band of the superconducting QR probe, and improved approaches to analyte detection using adaptive algorithms for resonance detection.

The use of an HTS material allows a relatively inexpensive cooling system to be used, such as liquid nitrogen. However any superconducting material may be used if cooling complexity and expense is not a major issue. The term HTS is used with the understanding that any superconducting material can be used.

In embodiments of the present invention, an apparatus for QR detection of an analyte comprises a pulsed excitation source and a high-temperature superconducting (HTS) QR probe. Preferably, the probe may have a Q-factor greater than 1,000, and in some embodiments the Q-factor may be greater than 10,000. In conventional pulsed QR, lineshape information is lost. However, the combination of pulsed excitation and narrow band probes allows lineshape information to be recovered, for example using a plurality of probe frequencies. This reduces false alarms, for example as signals with very narrow lineshapes (e.g. a few Hz) can be immediately rejected as noise.

High-temperature superconducting (HTS) QR probes were fabricated with Q-factors greater than 10,000. For these values of Q-factor, the bandwidth of the HTS QR probe is typically smaller than the bandwidth of the QR response. As an example, the bandwidth of the QR response of the explosive RDX is on the order of 500 Hz, the bandwidth of a normal metal probe is on the order of 30 kHz, while the bandwidth of the HTS probe is on the order of 300 Hz. As the center frequency of the RDX QR response is temperature dependent, and can vary on the order of 100 Hz per ° C., if the temperature of the explosive is unknown, it may be necessary to search for the QR response by varying the frequency of the HTS QR probe.

The term "HTS probe" is used generally to refer to a structure including a superconducting resonator, the term probe referring to a structure including one or more coils, such as a loop structure. Generally, HTS materials are used in the examples, but the invention is not limited to HTS materials.

Embodiments of the present invention include improved methods of probe frequency tuning. Using a high quality factor (Q-factor) probe for QR detection of an analyte, for example using a high-temperature superconducting (HTS) probe, trades improved signal-to-noise ratio for reduced detection bandwidth. In an improved QR detection system, an algorithm can be used to allow automatic search for a QR response by incorporating automatic frequency tuning of an HTS QR probe.

An example apparatus to assist detection of an analyte within a sample volume using QR comprises a superconducting resonator having a resonance frequency, a coarse frequency controller operable to adjust the resonance frequency of the superconducting resonator so as to be proximate to an expected response frequency of the analyte; and a fine frequency controller operable to adjust the resonance frequency over a frequency band including the expected response frequency of the analyte. Here, the terms coarse and fine are used relative to each other, the fine frequency control being capable of implementing smaller frequency steps of the resonance frequency. The apparatus may include a separate conventional (non-superconducting) excitation coil for exciting the QR response. In other examples, a superconducting resonator can be used for both excitation and as a receiver coil. A fine frequency controller may adjust the resonance frequency over the frequency band using a blind algorithm, for example using uniform frequency steps. Alternatively, the probe frequency may be adjusted over the frequency band to search for a maximum QR response of the analyte.

The lineshape of the QR response can be determined from data obtained at a plurality of resonance frequencies, even if the superconducting resonator has a linewidth less than the QR response linewidth of the analyte. Further, fine tuning the resonance frequency allows the probe to track a temperature dependent transition frequency.

A coarse frequency controller may includes a mechanism for changing a position of the superconducting resonator relative to a tuning component, for example using a mechanical displacement of the superconducting resonator relative to another resonator, a dielectric wafer, or other component.

Embodiments of the invention further include a QR apparatus having excitation using a low-Q exciter, such as a copper coil, and detection by a separate high-Q probe, such as an HTS probe. Q-spoiling can be used to dissipate excitation pulse energy. In other examples, an HTS resonator is used for both excitation and detection, for example using a spin-echo data collection. The apparatus may further include an active Q-spoiling system allows the probe response to relax rapidly following the excitation pulse, allowing improved QR detection. Cloaking techniques may be used to avoid coupling of the excitation and detector probes.

An adaptive method was used for tuning the HTS QR probe that resulted in higher detection performance per unit time than a blind search for a QR transition by systematically moving the HTS QR probe frequency across the spectral range of interest. Various search algorithms may be used. An example blind search may use equal search frequency steps across an entire expected frequency range. Other possible adaptive algorithms include Maximization of Energy from Single Signals (MESS), where a new probe frequency is chosen as an estimated QR transition frequency determined from measurements made at previous probe frequencies, and Minimization of Energy Estimate Covariance (MEEC), where a new probe frequency is chosen to minimize LS (least squares) covariance. An adaptive algorithm may be used to shorten detection times, relative to a blind algorithm.

An example apparatus to assist detection of an analyte within a sample volume using nuclear quadrupole resonance (QR) comprises a superconducting resonator having a resonance frequency, a coarse frequency control, a fine frequency control, and an electronic module that adjust the coarse frequency control so that the resonance frequency is close to the response frequency, and adjusts the fine frequency control locate the response frequency of the analyte within the frequency band. An excitation coil may be separate from the superconducting resonator. The electronic module, through the frequency controls, may use an adaptive algorithm to search for the QR response of the analyte, for example to maximize the energy of the QR response, or to minimize the covariance of the least-squares estimates of the lineshape parameters.

DETAILED DESCRIPTION OF THE INVENTION

Figure 1:
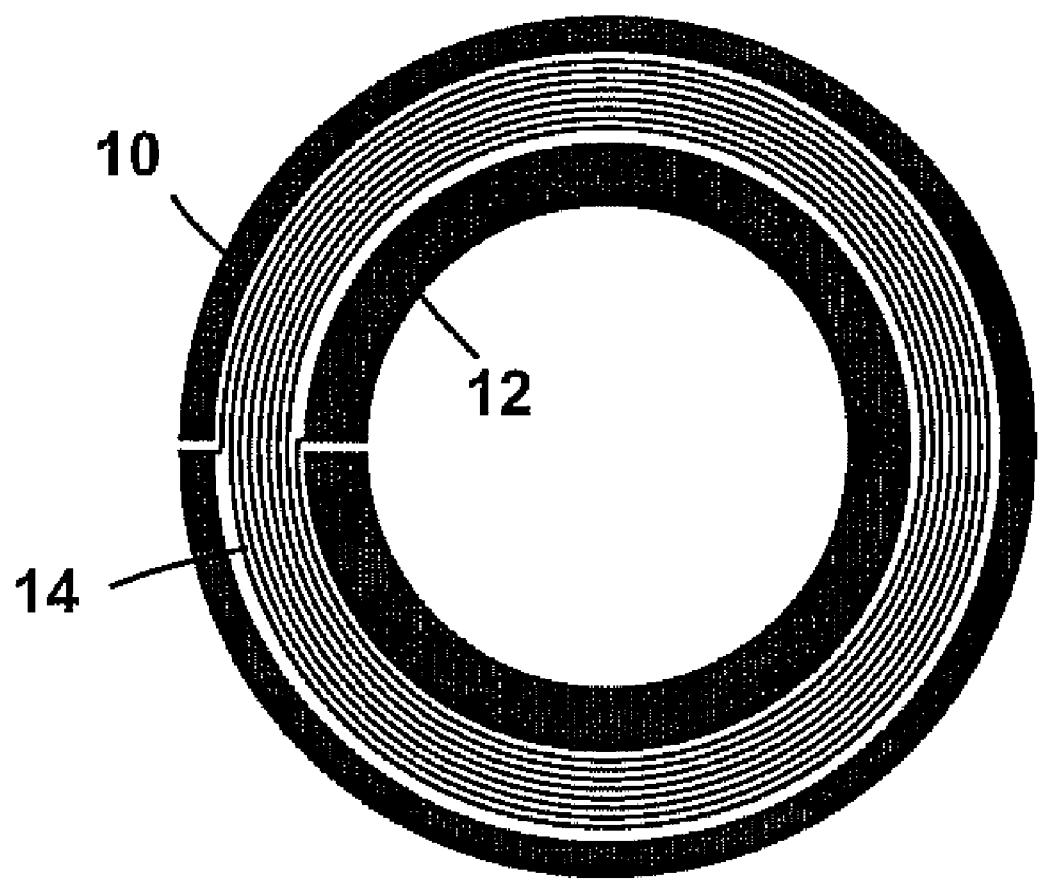
FIG. 1 shows a photolithography mask for patterning an HTS thin-film.

In pulsed or transient QR detection, a search region is subjected to a series of RF magnetic field pulses and a QR response is detected in the interval between the RF pulses. An apparatus broadcasts short duration radio frequency (RF) pulses using a transmitter coil, and if a target compound (analyte) is present, an RF signal is received by a receiver coil during the interval between the applied pulses. The transmitter coil (normal metal or superconducting) and receiver coil may be the same coil (normal metal or superconducting), or separate coils.

An QR signal originates from analytes with nuclei that have a nuclear quadrupole moment, such as nitrogen-14 (the common isotope of nitrogen). The QR response from each nitrogen compound has a distinct spectral signature, so that a QR detection system can discriminate among different analytes. In particular, QR can distinguish between types of explosives, such as RDX and TNT, and distinguish them from benign nitrogen compounds as t Examples of the present invention include a QR probe with a high Q-factor, which enhances sensitivity, and also reduces electrical interference when the interfering RF source lies outside the bandwidth of the QR probe. A QR probe was designed having a Q-factor greater than 10,000, providing greater than a ten-fold increase in explosives detection sensitivity using QR. High-temperature superconducting (HTS) resonators were used to fabricate QR probes with significantly higher Q-factors than those obtainable with normal metal (non-superconducting) probes. The high Q-factor of the HTS QR probe not only increases the level of the received QR signal, but also effectively attenuates both internal and external sources of RP interference that are not within the pass-band of the HTS probe.

The power handling capabilities of an HTS resonator can be increased by using wider line widths and increasing the separation between the turns. Constraining the electric field within a low loss dielectric of the resonator allows achievement of high-Q factor resonators. As a result, dual sided HTS resonators have significantly higher Q-factors than single-sided resonators. A QR response was detected using an HTS probe for both excitation and detection, and using a conventional excitation coil and an HTS probe for reception.

Conventional apparatus use the same probe for excitation and detection, leading to sub-optimal detection performance. Apparatus according to some embodiments of the present invention use an excitation probe and a separate detection probe. A low Q-factor excitation probe maintains the impedance match between the transmitter and excitation probe for maximum power transfer, despite the presence of material within the search region that may electrically couple to the excitation coil. A high Q-factor detection probe maximizes the signal-to-noise ratio of the QR measurement. The detection probe uses a high-temperature superconductor (HTS) resonator that provides a Q-factor that is more than two orders of magnitude greater than for QR probes fabricated from normal (non-superconducting) metals. A QR response was detected for the first time using a non-superconducting metal excitation probe with a low Q-factor, and an HTS detection probe with a high Q-factor.

A cryogenically cooled quadrupole resonance probe was developed with a quality factor on the on the order of 20,000 during detection. The probe's high Q-factor improved the signal-to-noise ratio by more than an order of magnitude compared to non-superconducting probes. Example probes includes self-resonant circuits fabricated from a high-temperature super-conductor on a low-polarization loss substrate. The probe was tunable over a wide frequency range, and the probe's natural response to the excitation pulse was dissipated. The resulting quadrupole resonance probe has a quality-factor on the on the order of 20,000 during detection.

Embodiments of the present invention include apparatus that overcome problems such as limited operating temperature range, and electrical interference from both internal and external RF sources. When the bandwidth of a QR probe is smaller than the bandwidth of the QR response, it is possible to attain a higher SNR measurement than with a probe of greater bandwidth. Also, when the bandwidth of the QR probe is smaller than the bandwidth of the QR response, the spectra of a QR measurement contains distinct peaks corresponding to the QR response and the HTS QR probe. In contrast, when detecting QR signal using a low Q-factor probe, the spectra of the received signal is nearly identical to the spectra of the QR response.

The detection performance of a QR system using a probe whose bandwidth is less than that of the QR response may use an algorithm for tuning the probe frequency through a spectral region corresponding to the expected temperature range of the analyte QR response. The line-shape of the QR response can be recovered from multiple measurements obtained with a QR probe whose bandwidth is smaller than that of the QR response. This can be used to eliminate noise signals, which typically have much different lineshapes to a genuine QR resonance of the analyte. The presence or absence of an expected QR line-shape, obtained from multiple measurements using a narrowband QR probe, allows a reduction in the false alarm rate of a QR detection system. For example, the coarse frequency control can be used to adjust the resonance frequency to a value close to that expected for an analyte QR resonance, and the fine frequency control can then search for an analyte resonance using an algorithm to help locate the peak.

One approach for improving the SNR of QR detection experiments is signal averaging through the coherent addition of multiple QR responses. This presents a tradeoff between detection time and increased SNR, as the SNR increases with square-root of the number of averages, and hence detection time. In order to achieve a large SNR improvement through signal averaging, the following conditions are preferably met. First, the noise is uncorrelated, and second, certain RF pulse sequences that generate multiple QR responses for averaging, most notably SORC and PAPs-NPAPs, require precise knowledge of the center frequency of the QR response in order to achieve coherent addition of the QR responses. In practice, the noise present within the detection pass-band is partially correlated, and so there is a limit in the maximum SNR that can be achieved through averaging. Furthermore, because the spectral locus of the QR response is temperature dependent, the precise center frequency of the QR response is unknown. For these reasons, signal averaging does not provide a complete solution for increasing the SNR of QR measurements.

Another approach for improving the SNR of QR measurements is to increase the quality-factor (Q-factor) of the QR probe. The SNR of a nuclear resonance measurement is proportional to the square-root of the Q-factor. QR detection systems using normal (non-superconducting) probes have Q-factors on the order of 100. Hence, an increased probe Q-factor improves the SNR of QR measurements.

HTS Resonator Fabrication

FIG. 1 shows a photolithography mask used to produce a resonator. Resonators were fabricated on 0.5 mm thick, 50 mm diameter lanthanum aluminate wafer coated on both sides by a film of the thallium-based high temperature superconductor (HTS) material $Tl_2Ba_2CaCu_2O_8$ (thallium-barium-calcium-copper oxide, TBCCO). Films were formed using a sputter deposition of an amorphous precursor film, which does not contain thallium, on the front and back surfaces of the wafer. A subsequent high temperature anneal in a thallium oxide partial pressure forms the epitaxial superconducting phase. The resulting 0.6 micrometer TBCCO films have a critical temperature above 102 K and a surface resistance of 300 mieroohms measured at 10 GHz.

The wafer was then patterned into a self-resonant device. The design achieved a desired resonant frequency based on numerical electromagnetic simulations. The mask was exposed on both sides of the wafer with the resulting HTS layers mirrored about the plane of the substrate wafer. As a final step, a thin protective layer of Teflon™ AF was applied to both sides of the finished device. The resulting device is a distributed parameter electrical circuit with multiple resonant modes. The inner and outer annular rings on the HTS mask are patterned opposite one another on both sides of the wafer, forming parallel plate capacitors. The spirals connecting the annular rings each have self inductance and they share mutual inductance as well. Additional inductance and capacitance is distributed throughout the HTS resonator features; for example, the turns of a spiral are capacitively coupled.

The structure of FIG. 1 comprises of a thick outer ring (10) and a thick inner ring (12), with an 8 turn spiral (14) connecting the rings. The same structure is etched on opposite sides of a wafer, with the spirals in opposite directions so that the currents are oriented in the same direction for both spirals. The spirals form an inductance, and are terminated with slit annular rings that form an inner and outer capacitance together with the high permittivity, low loss, wafer dielectric.

The superconducting material presents some small loss, and the resonator may be modeled as a series RLC circuit. A lumped-parameter RLC model may be used as the electrical length of the spirals was less than 25 degrees at the operating frequencies used.

Frequency Tuning of HTS OR Probe

An example HTS QR probe comprises at least one HTS resonator whose frequency is determined by the geometry of the resonator and the electromagnetic environment surrounding the resonator. As the bandwidth of the HTS resonator is typically smaller than that of the QR response, and the frequency of the QR response is temperature dependent, the QR probe frequency can be varied in order to search for a QR response. Several mechanisms for adjusting the frequency of an HTS probe were developed, and these methods can be categorized as either coarse or fine tuning methods.

Coarse tuning of an HTS resonator may use mechanically adjustment, for example through electrical coupling an HTS resonator to a low-loss dielectric wafer, and/or coupling to a second resonator (conventional resonator or HTS resonator). Varying the proximity of a dielectric wafer to an HTS resonator produces a net change in the self-capacitance of the HTS resonator, thereby effecting a change in resonant frequency. Electrical coupling between two HTS resonators results in two resonant peaks whose locations are varied by adjusting the mechanical displacement between the two resonators. Capacitors allow distributed capacitive coupling between the turns of a single coil.

Fine tuning can be accomplished by magnetically coupling the HTS resonator to a second resonant circuit formed by a loop surrounding the resonator, called a control loop, and an external capacitance. The control loop may be non-superconducting metal (such as copper), or a superconducting metal loop which avoid lowering the Q-factor of the HTS probe by reducing eddy-current losses in the control loop. Varying the external capacitance can electrically control the frequency of the HTS probe. The resonant frequency of the circuit is determined by its inductance and capacitance. Thus, tuning the circuit resonant frequency is accomplished by changing either the inductance and/or capacitance. For the HTS resonator, this corresponds to changing the amount of energy stored by the resonator in either its magnetic field and/or its electric field.

Unless otherwise stated, tuning methods were tested using an HTS resonator with a primary mode at 4.345 MHz and an unloaded Q-factor of 700,000. During measurements, the probe was cooled by immersion in liquid nitrogen, which has a relative permittivity of about 1,546. Resonance frequencies were measured using a VNA set to measure transmission coefficients. Further details on tuning methods are given below.

Permittivity Tuning

A resonator was fabricated on a 50 mm sapphire wafer, having a design based on Withers et al., "Thin-film HTS probe coils for magnetic-resonance imaging. IEEE Transactions on Applied Superconductivity, 3(1):2450-2453, 1993. The resonator had a resonant frequency of 3.549 MHz and a Q-factor of 400,000. In this example, a significant portion of the resonator's electric field exists outside the resonator structure, making it amenable to permittivity tuning. Placing a 0.5 mm thick, 50 mm diameter c-axis sapphire wafer in direct contact with the HTS resonator lowered the resonant frequency to 3.449 MHz, a change of −100 kHz, while having no measurable impact on Q-factor.

For permittivity tuning experiments, an HTS resonator was placed in direct contact with a 0.5 mm thick, 50 mm diameter c-axis sapphire wafer. Sapphire has a relative permittivity of 11.5 parallel to the c-axis and 9.4 perpendicular to the axis. The resulting change in resonant frequency was −12 kHz, with the lower resonant frequency due to increased capacitance. The experiment was repeated using a similarly dimensioned lanthanum aluminate wafer. Lanthanum aluminate has a relative permittivity of 24.5. The resulting change in resonant frequency was −25 kHz. As both sapphire and lanthanum aluminate have loss tangents comparable to the surrounding liquid nitrogen, no change in the resonator's Q-factor was observed.

Tuning was accomplished by changing the relative geometry of the two wafers. A test fixture was used that allowed variation of the overlap of the wafers while maintaining a similar gap distance. Zero displacement corresponds to maximum overlap.

Figure 2A:
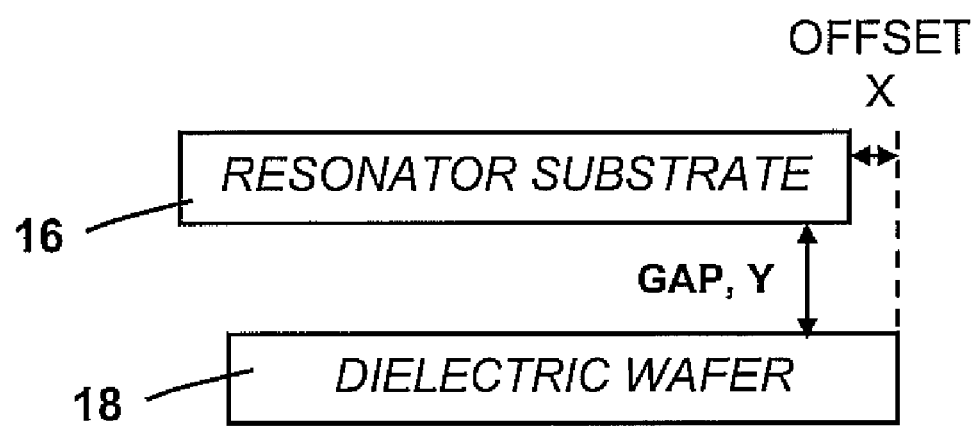
FIG. 2 shows experimental results from tuning an HTS resonator using a high permittivity wafer.

FIG. 2A illustrates the relative displacement of the two wafers. In this example, two disk-shaped components (resonator substrate 16 and dielectric wafer 18) were displaced relative to each other by a distance X, while maintaining the same gap or axial separation Y. In alternative approaches, the gap may be adjusted, or the relative orientation modified so that non-parallel configurations are obtained.

Figure 2B:
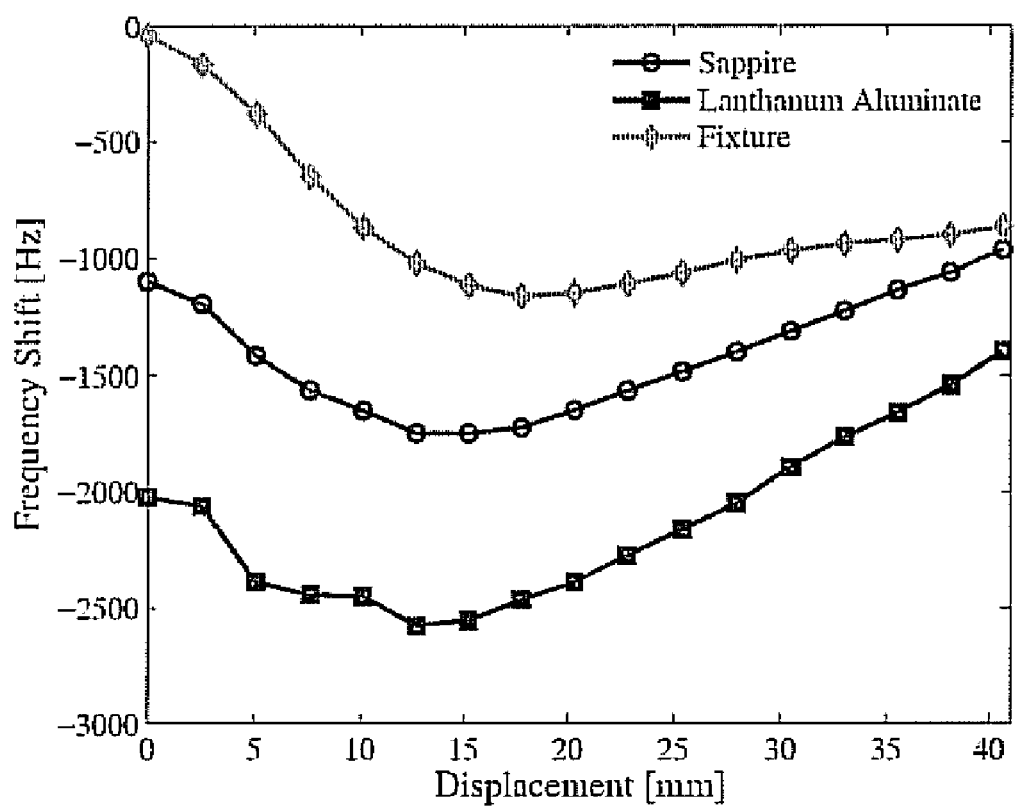

FIG. 2B shows a resonator tuned by varying a relative displacement, where the "Fixture" tuning results represent permittivity tuning by the composite material of the fixture (Garrolite G10). The lower curve represents lanthanum aluminate, the middle curve represents sapphire, and the upper curve represents the fixture material.

The two wafers were separated by 1.75 mm, and this distance can be modified to adjust tuning range. All three curves initially trend downward indicating increased capacitance. In the cases of the sapphire and lanthanum aluminate wafers, this seems counterintutive as the permittivity of the G10 is lower than the wafers. However, the gap between the resonator and the G10 of the fixture is about 0.75 mm placing the fixture about 1 mm closer than the high permittivity wafers. The reduced gap results in the resonator's electric field having more interaction with the G10 than with the wafers, compensating for the lower permittivity of the G10.

Hence, permittivity tuning of an HTS resonator can be achieved using by changing the dielectric environment of the HTS resonator, for example using a proximate dielectric element, such as a dielectric wafer. Tuning can be achieved by changing the relative position (including position and/or orientation) of the dielectric element relative to the resonator, for example by changing a gap distance, overlap of planar structures, and the like, or some combination thereof. More than one dielectric element may be used, one or more of which can be adjustable. The permittivity of the dielectric element may be modifiable, for example using an electric field, variable composition, use of shielding components, or other process. The permittivity of the environment of the resonator may also be adjusted, for example using different fluid compositions surrounding the resonator.

Tuning with Shielding Currents

When the HTS resonator is in proximity with a conductor, the resonator's magnetic field induces shielding currents in the conductor. These shielding currents give rise to their own magnetic field that opposes the resonator field, lowering the magnetic energy stored in the HTS resonator. In terms of the circuit model, this decreases the circuit's inductance. While any conductor supports shielding currents, conductor losses would negatively impact the HTS resonator's Q-factor. To avoid this, the same HTS material can be used in fabricating other coupled resonators.

Figure 3:
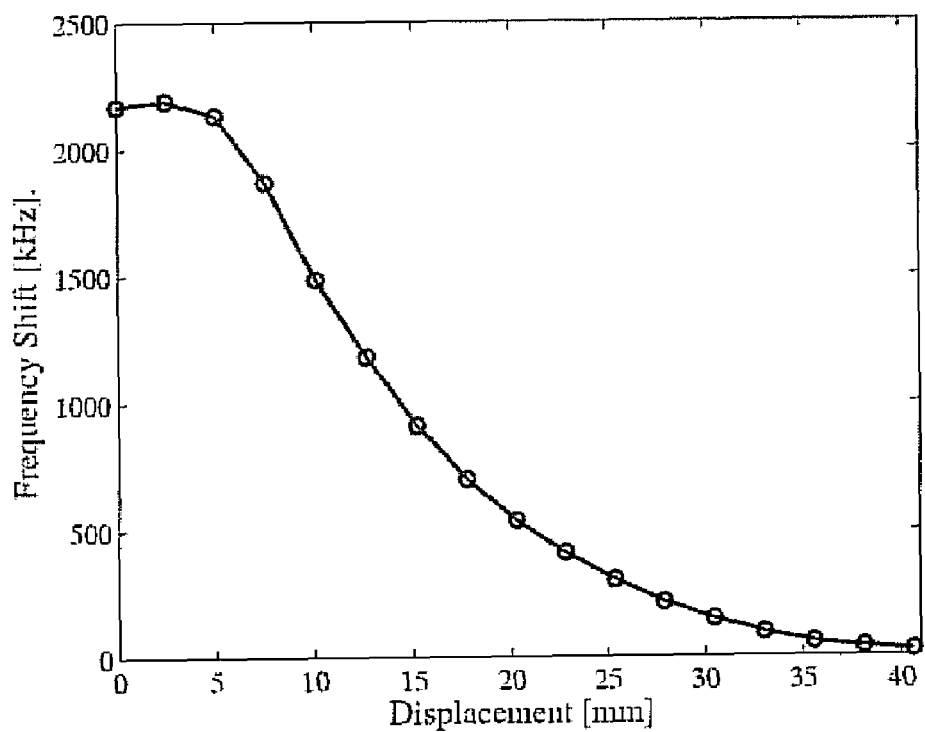
FIG. 3 illustrates tuning an HTS resonator using an unpatterned HTS wafer.

The experimental arrangements were similar to those used in permittivity tuning experiments. An HTS coated lanthanum aluminate wafer was placed in a stationary mount of the test fixture. The same HTS resonator used in the permittivity tuning experiment is also used for this experiment in the moving mount. As the resonator is moved, it experiences some dielectric tuning from moving over the fixture in addition to the shielding current tuning. However, the magnitude of this effect is negligible compared to the effect of the shielding currents. The position 0 mm indicates that the two wafers are fully overlapped. The results of a typical experiment are shown in FIG. 3.

In this example, the tuning range was 2.2 MHz covering the frequencies from 4.3 MHz to 6.5 MHz. In terms of an RLC equivalent circuit, this corresponds to reducing the inductance of the circuit by more than half its untuned value. This tuning method provides a tuning range useful for QR probe applications. However, if an unpatterned HTS wafer is interposed between the HTS resonator and a signal source, the resonator may become insensitive to the source.

Tuning by Coupling to Another Resonant Circuit

Figure 4:
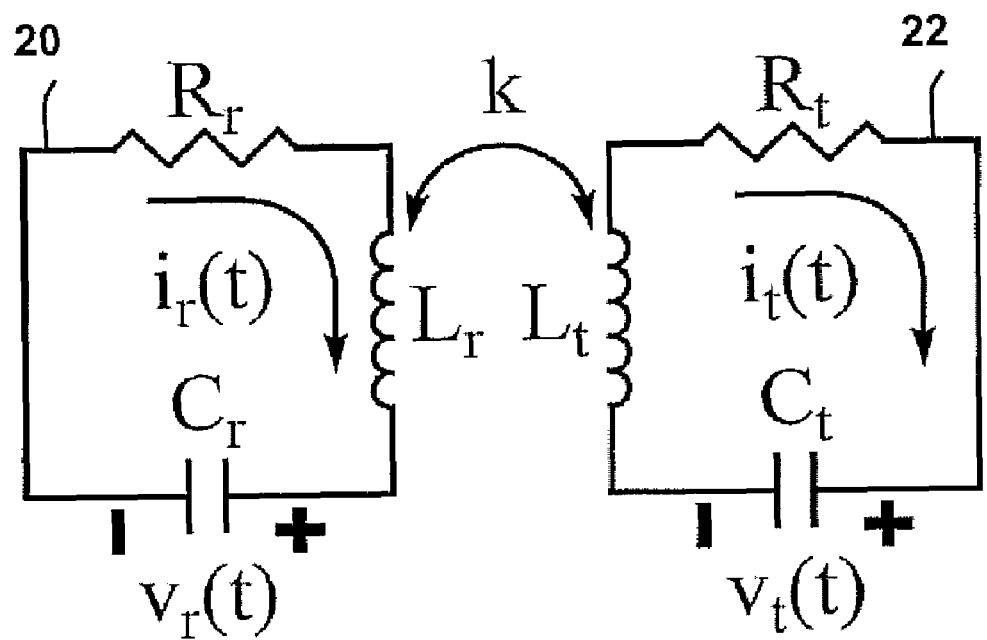
FIG. 4 shows two resonant RLC circuits coupled magnetically.

FIG. 4 shows two resonant RLC circuits (20 and 22) coupled magnetically. For a general case when the inductive coupling is less than unity, the resulting circuit may have two resonances. Using a change of variable to express the characteristic equation in a normalized form [E. J. Burge, "Definitions of resonance and exact conditions for resonance in some electrical circuits. II. tuned coupled circuits", American Journal of Physics, 29:251-256, 1960], analytic expressions are derived that accurately approximate the system's resonant frequencies.

Letting $$p^4 = j^4 \frac{\omega^4}{\omega_r^2 \omega_t^2}, \quad (1)$$

then for large Q-factors $$\omega_{x,y} = \sqrt{-\omega_r \omega_t p_{x,y}^2} \quad (2)$$

$$= \sqrt{\frac{\omega_r^2 + \omega_t^2 \pm \sqrt{(\omega_r^2 + \omega_t^2)^2 - 4\omega_r^2 \omega_t^2 (1 - k^2)}}{2(1 - k^2)}}$$

When the inductive coupling is zero, the resonances of the individual circuits are unaltered. As the coupling increases, the resonances are pushed further apart in frequency. The amount of the change in resonant frequency is determined largely by the proximity of the individual circuit's resonant frequencies. The closer together the individual resonances start, the further they push apart as inductive coupling increases. Thus, tuning by this method can be accomplished in two different ways: changing the coupling between the resonant circuits or changing the resonant frequency of one of the circuits.

Tuning was achieved by changing coupling. Two resonant circuits can be used to alter each other's resonant frequency, for example using a first an HTS resonator to tune a second. Tuning can be implemented by changing the inductive coupling of the two resonators.

The experimental arrangements used a second HTS resonator with resonance mode at 3.608 MHz and has an unloaded Q-factor of 673,000. The same HTS resonator used in the previous tuning experiment was used for this experiment in a moving mount. The position 0 mm indicates that the two resonators are fully overlapped. Because of the geometry of the resonators, the inductive coupling is expected to be highest in this position.

Figure 5:
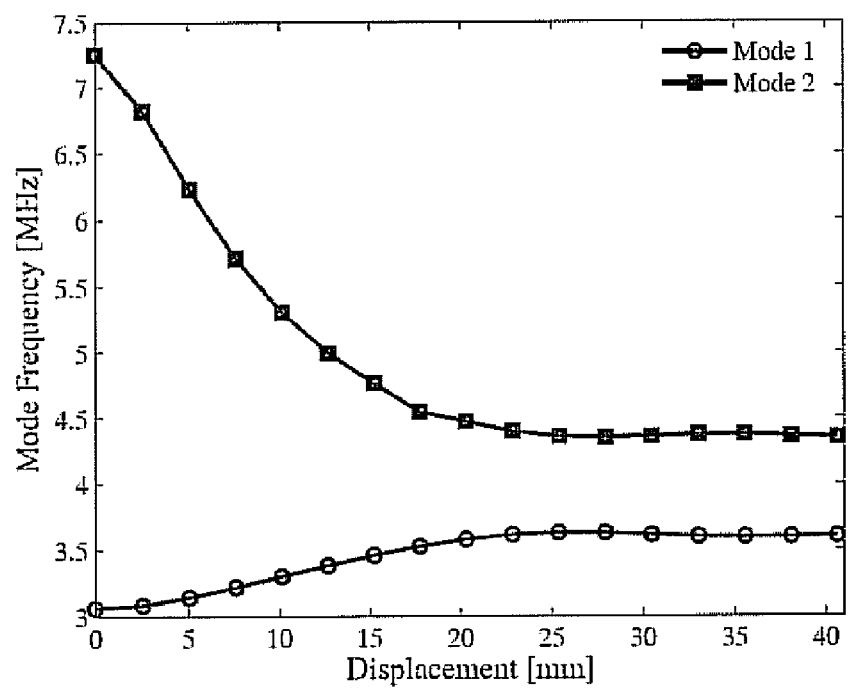
FIG. 5 illustrates the tuning of an HTS resonator by varying its inductive coupling to a second HTS resonator.

The results of a typical experiment are shown in FIG. 5, illustrating tuning an HTS resonator by varying its inductive coupling to a second HTS resonator. As the overlap is reduced, the inductive coupling generally decreases, however, the decrease is not monotonic. There is a small, brief rise in coupling around 35 mm due to the overlap of the resonator's spirals. The tuning range achieved is significant, with the lower mode covering the 600 kHz below 3.608 MHz and the upper mode covering 1.9 MHz above 4.345 MHz. These ranges cover both the three v+ and three v− transitions of RDX. The impact of permittivity tuning was negligible. The lower mode data was well fitted by theory, however, it begins to consistently underestimate the resonant frequencies as the coupling increases. This is due to the fact that the geometry between the two resonators is not constant with frequency. As the wavelength shortens, the resonators become electrically larger and closer together improving their coupling. Since the inductive coupling was derived from the measurements at the upper modes, these results may overestimate the inductive coupling at the lower mode. In other approaches, a variable gap distance or other change in relative position (such as relative angular orientation) may be used.

Tuning by Changing Resonant Frequency

Figure 6:
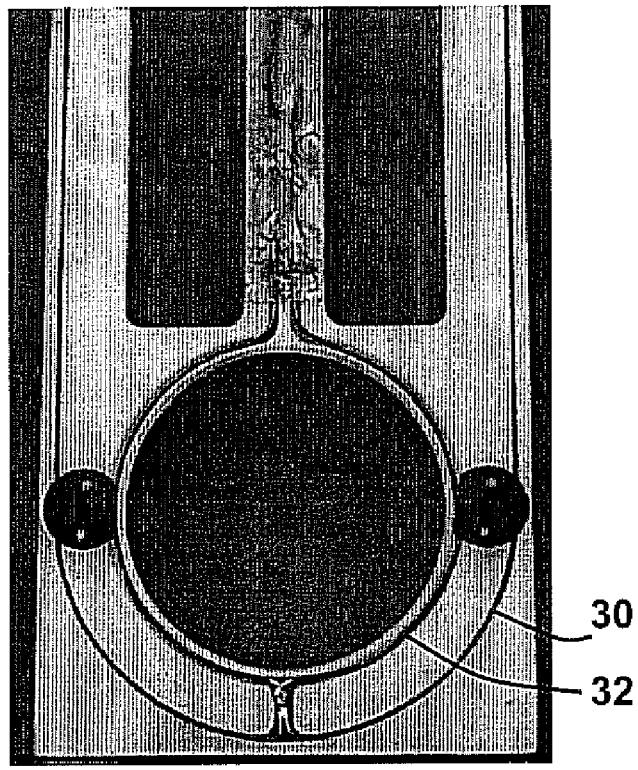
FIG. 6 shows a control loop integrated on a test fixture.

A conventional resonant circuit was used to tune the HTS resonator. FIG. 6 is a photograph of a fixture including two connected copper loops (30 and 32) located around the perimeter of an HTS resonator when supported in a stationary mount. Only the inner loop (32) was used, which had a diameter of 53.35 mm, for purposes of tuning. This may be called a control loop, as it allows control of various aspects of the probe behavior, such as resonance frequency, Q-factor, and the like. The control loop may also comprise a superconducting material, to avoid observed Q-factor reductions when Q-spoiling is not desired. Resistors or other components may be switched in series and/or parallel with a control loop using any appropriate switching device. The outer return loop 30, whose circular portion has a radius of 35.56 mm, is connected to the bottom of the inner loop; it is not used in tuning and is discussed further below.

The inner loop has fixed geometry relative to the HTS resonator and so inductive coupling is not controlled in this example. The inner loop was resonated at different frequencies to tune the HTS resonator mode. A bank of seven capacitors were switched in series with the inner loop, allowing a total of 128 different frequencies to be selected over the tuning range. This example is not limiting, as other combinations of capacitors, or variable capacitors, may be used.

Figure 7:
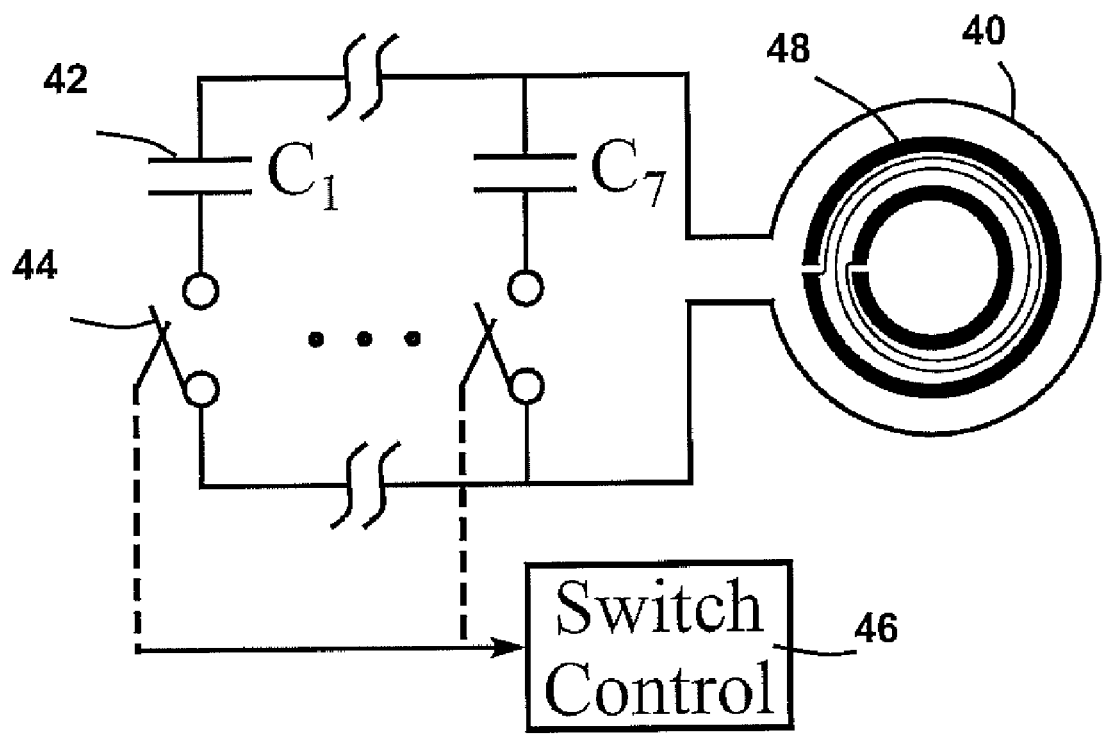
FIG. 7 shows a non-HTS resonant circuit used to tune an HTS resonator.

FIG. 7 shows an example schematic for a fine tuning circuit. In this example, a conventional (non-superconducting) resonant circuit is used to tune an HTS resonator. The resonant circuit comprises capacitors such as capacitor 42, with associated switches such as switch 44, and a loop 40 that surrounds the HTS resonator 48. The switch control 46 switches the capacitors $C_1$-$C_7$ in or out of the resonant circuit, allowing fine tuning of the HTS resonator 48.

Figure 8:
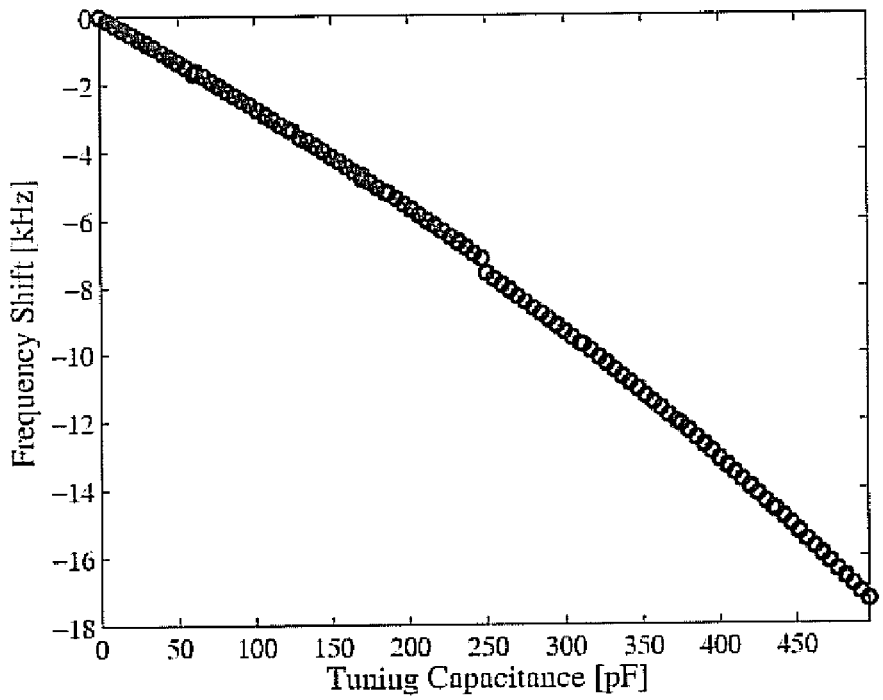
FIG. 8 shows experimental data for tuning an HTS resonator by varying the resonant frequency of a coupled conventional resonant circuit.

Typical experimental results using the circuit of FIG. 7 are shown in FIG. 8 with the change in resonant frequency plotted against the nominal series capacitance. The slight discontinuity in frequency change at 250 pF is due a slight mismatch between the capacitance from the sum of the lower six capacitors and the capacitance of seventh capacitor.

The probe Q-factor is significantly reduced, due to the dissipation of the shielding current induced into the control loop by the HTS resonator. In one example, a control loop was placed around an HTS resonator with a Q-factor of 844,800 and a resonant frequency of 4.346 MHz. The resulting resonant frequency increased by 910 Hz due to shielding currents, however, the Q-factor fell to 76,250 due to the resistive losses in the copper wire. Changes due to various portions of the control loop are shown in Table 1 below:

TABLE 1

| Test Condition | Q-factor | Δf (Hz) |
| --- | --- | --- |
| No control loop | 844,750 | 0 |
| Outer loop, no leads | 432,750 | 102 |
| Inner loop, no leads | 103,500 | 699 |
| Inner and outer loop, no leads | 77,500 | 1093 |
| Complete control loop | 76,250 | 910 |

The table entries indicating "no leads" mean that the wires have been cut parallel to the top of the inner loop. Note that the resonant frequency shift caused by the completed control loop is about 100 Hz lower that the shift due for the loops without the leads. This reduction is caused by the increased capacitive coupling especially between the inner leads. The dissipation of shielding current by the control loop largely limits the HTS probe's Q-factor.

The dissipation of shielding current by the control loop largely limits the HTS probe's Q-factor. In other examples, the copper control loop may be replaced with an HTS control loop.

The shielding currents induced in the HTS wafer were large enough to shift the HTS resonator's mode by 2 MHz while not having a measurable impact on the Q-factor. The probe fixture material can also be selected to serve as the substrate for an HTS control loop. For example, the fixture may be fabricated from a low polarization loss material that is compatible with the growth of an HTS thin film.

Relays were used to complete the circuit between the capacitor and the loop with very low resistance when they are on, and to provide a very high impedance when they are off. While their switching time offers improvements over mechanical tuning, it is still long compared to the typical spacing of pulses in a multi-pulse QR excitation sequence. Other fast switching mechanisms may be used. While FET switches with on state resistances comparable to relays are available, their drain-source capacitance in the off state may be too large to appear open circuit in the nitrogen-14 transition band. Diodes may present the opposite problem in that off state capacitance is small enough to appear open circuit while the on state resistance is too large to be practical. A new generation of PIN diodes are suitable for operation with the nitrogen-14 transition band. The PIN diodes combine fast switching with low on state resistance and minimal off state capacitance.

As the loop's mode is brought closer in frequency to that of the HTS resonator, the increased interaction which produces tuning also causes the resonators to increasingly share their electrical losses. The losses in the resonant loop are due to the resistance losses of the conductors and the polarization losses in the capacitors. Conductor losses were kept low using copper wire and by using relays for switching, and polarization losses in the capacitors kept low using silver mica capacitors. However, as the loop inductance is low, the need for low loss capacitors precludes resonating the loop at frequencies below the HTS resonator's mode. This limits the loop to tuning the probe to lower frequencies only.

The loop Q-factor was still more than two orders of magnitude less than the probe un-tuned Q-factor of 80,000. Tuning causes the Q-factor of the HTS probe to deteriorate further as more losses are coupled to the resonator.

In other examples, an HTS probe may be tuned by inductive coupling with a second resonator, adjustment being obtained using any other approach such as adjusting relative positions, number and position of shielding elements, second resonators having tunable frequencies obtained by any other method, and the like.

Tunable HTS Probe

By combining mechanically controlled tuning with a second HTS resonator and electronically controlled tuning with a conventional resonant circuit, an HTS probe is achieved that is capable of working over a wide frequency range and has sufficient fine tuning to maximize the measured QR response.

Q-Spoiling an HTS Probe

The applied magnetic field that excites the QR nuclei also stores energy in the HTS probe. Following an RF pulse, the residual energy stored in the HTS probe may obscure the weak QR signal induced in the HTS probe. For this reason, immediately following the application of a RF pulse, it is useful to temporarily, and significantly, reduce the Q-factor of the HTS probe so that the residual energy dissipates at a rate much faster than the relaxation time of the QR signal, particularly when excitation and reception are performed using the same probe. This operation, called Q-spoiling, is affected by coupling an electrically lossy network to the HTS probe through the control loop surrounding the HTS resonator.

The probe's natural response allows this energy to decay. For example, a conventional probe, whose Q-factor is on the order of 100, would have a relaxation constant of $-\tau=9.33$ microseconds when tuned to the ν– transition of RDX at 3.410 MHz. This relaxation constant increases directly proportional with the probe's Q-factor. The probe natural response has a much larger initial magnitude than the QR response and, as the probe decay constant grows in duration, the probe response may completely obscure the QR response.

By temporarily reducing the probe Q-factor, following the excitation pulse, this allows the probe's natural response to relax more rapidly and to take advantage of the HTS probe Q-factor during the receive window.

Figure 9:
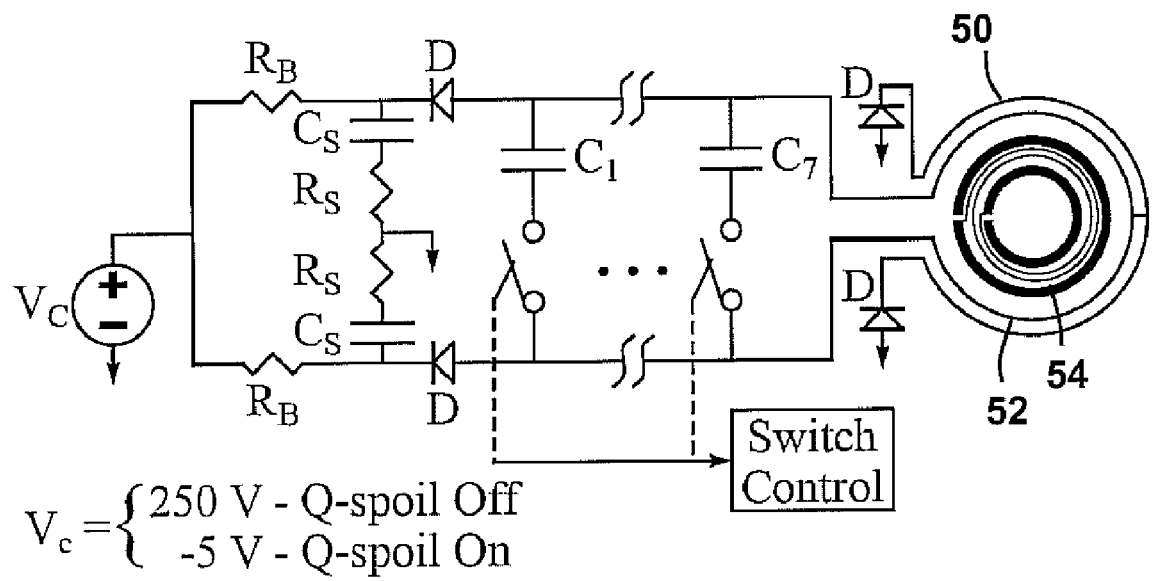
FIG. 9 shows a schematic of a Q-spoil and tuning network.

FIG. 9 is a schematic of an example circuit used to implement Q-spoiling. A control loop 52 was used to inductively couple the ITS probe to an intentionally lossy tuned circuit, giving a temporary reduction in Q-factor. The capacitance switching circuit with switch control is similar to that discussed above in relation to FIG. 7.

The switching transient associated with turning the Q-spoil circuit off may adversely affect the measurement of the QR response. This is not a problem for the tuning circuit as the tuning was switched well prior to the receive window allowing its transients to dissipate naturally. While the switching transients cannot be avoided, the transient currents can be balanced, reducing their impact. The outer loop 50 of the control loop serves as a balanced ground path for the circuit.

The resonant frequency of the control loop for Q-spoiling is determined by the series combination of the two capacitors labeled $C_S$. The two resistors labeled $R_S$ provide the circuit with additional losses that serve to lower the overall Q-factor of the probe. The four diodes labeled D are ultra-fast recovery diodes and are used to isolate the Q-spoiling elements from the control loop when Q-spoiling is not required. The two resistors labeled $R_B$ serve to set the diode's bias current during Q-spoiling. The source labeled $V_S$ provides the bias voltage for the diodes. When Q-spoiling is active, $V_C=-5$ V allowing the diodes to conduct. When Q-spoiling is inactive $V_C$=250 V; this value was chosen to ensure that the diodes do not conduct during the excitation pulse. Also, $V_C$=0 V corresponds to receive mode The circuit includes switched capacitances $C_1, \ldots C_7$, as discussed above in relation to FIG. 7. The use of 8 capacitors allows an 8-bit word to control the tuning frequency, however other numbers of capacitors or a variable capacitor may be used. The circuit may include an additional variable capacitor available for manual fine tuning. The value of the actual frequencies depends on the values of the capacitors in the network. Each successive capacitor was chosen to be twice as large as the previous: $C_n 32\ 2C_{n-1}$, within the limits of available capacitor values. This allows a binary control signal from the switch control to tune the probe in a roughly linear fashion, with the tuning offset being inversely proportional to the value of D (binary value) relative to the value at D=0. An example configuration used: $C_1$=5 pF, $C_2$=10pF, $C_3$=15 pF, $C_4$=30 pF, $C_5$=62, $C_6$=120 pF, and $C_7$=250 pF. These capacitor values do not exactly follow the doubling rule, and hence the frequencies are not uniformly spaced, due to limited commercial availability of capacitor values.

The capacitors are connected across the control loop and can be switched in out electronically using relays or other switches. In this example, the relays are driven by TTL lines that form a 7-bit word referred to as D. The smallest capacitor, $C_1$, is driven by $D_0$, the least significant bit of D, and imparts the smallest change in frequency. Likewise, the larger capacitors are switched by the consecutive control bits $D_1$ trough $D_7$. This configuration was chosen to provide a reasonable range (about 15 kHz) but also to provide sufficient frequency resolution to achieve meaningful results, with about 47 values lying in the range 3.757 MHz±3 kHz.

A look-up table was used to choose a D value closest to the desired frequency. Also, the probe was pinged to determine its exact frequency, which may vary due to varying environmental factors. The look-up table may be updated in real-time using the most recent measurements.

An HTS resonator formed a probe with a quality-factor of about 20,000 when the tuning bit $D_7$ was enabled and the probes are tuned to about 3.757 MHz. The resulting probe bandwidth is about 200 Hz. A differential amplifier was used to access the signal as the differential voltage induced across leads from the control loop. This setup was chosen to reduce detriment to the quality factor. Experiments were performed using sodium nitrite as the sample material, which has a transition frequency at 3.757 MHz at 77 K with a FWHM of around 1 kHz.

When Q-spoiling is active, the resulting system can be modeled as two magnetically coupled circuits, as discussed above in relation to FIG. 4. For Q-spoiling, the circuit coupled to the resonator is made intentionally lossy. A possible design objective is to choose the Q-spoiling circuit's resonant frequency and Q-factor so that the combined fourth order system dissipates its stored energy as rapidly as possible. These values may be found be determining the roots of the system's characteristic equation.

The Q-factor can be found from the following equation, where the terms p are defined as discussed above in relation to Equations 1 and 2 for the two resonant circuits:

$$Q_x = \frac{\sqrt{p_1 p_2}}{p_1 + p_2} \qquad (3)$$

Figure 10:
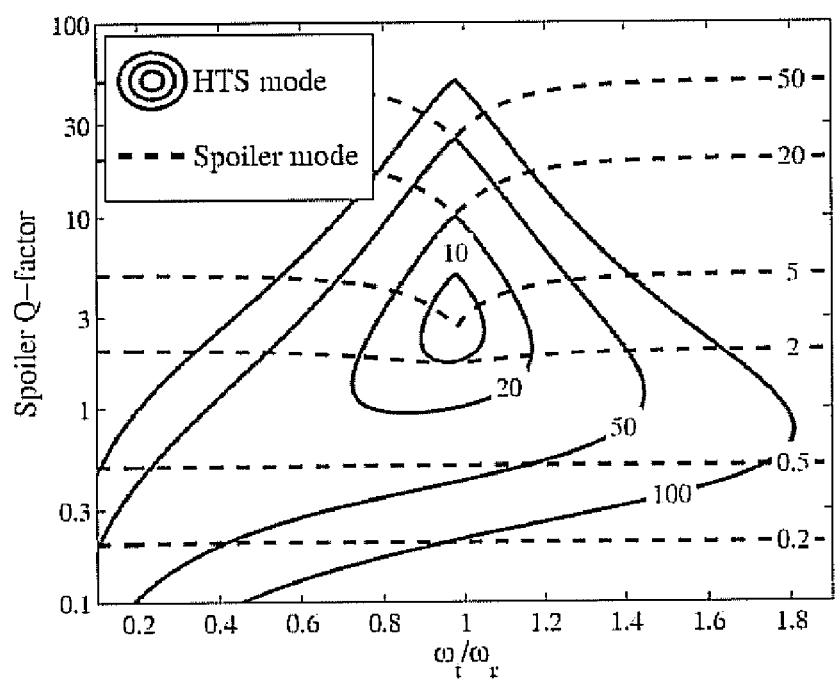
FIG. 10 illustrates contours of constant Q-factor for two modes of a Q-spoiled resonator modes, for k=0.216.

FIG. 10 shows contours of constant Q-factor for the two second order terms of the spoiled system, plotted as a function of the spoiler's Q-factor and the ratio of the spoiler's and the HTS resonator's resonant frequencies. The figure's legend identifies the origin of the two modes, the HTS resonator and the Q-spoil circuit. This plot uses k=0.216 for the inductive coupling, which was measured for this configuration. The minimum Q-factors for the two terms occurs near the inflection in the spoiler mode's Q-factor=5 contour, however, in practice the HTS mode's Q-factor=100 contour encloses a wide range of adequate results.

The inductive coupling plays an important role in determining both the minimum Q-factors that may be obtained and the range of tuner circuit parameters that produce acceptable results. As the coupling decreases, the minimum attainable Q-factors increases and the range of acceptable circuit parameters decreases. For k=0. 173, the range of acceptable circuit parameters to achieve results inside the HTS mode's Q-factor=100 contour decreases substantially.

In a representative system, the control loop inductance is Lt=605 nH, the Q-spoil capacitances are each 4200 pF giving Ct=2100 pF, and the Q-spoil resistances are each 1. 2Ω which, in addition to the wire resistance, makes Rt=3 ohms. Computing the resonant frequency and Q-factor for the Q-spoil circuit results in ft=4.465 MHz and Qt=5.66. To test the effectiveness of the Q-spoil system, an FITS resonator was placed in the fixed mount of the probe fixture and used a separate loop to power match a transmitter to the resonator when it was unspoiled. In this configuration, the HTS resonator resonant frequency is 4.346 MHz and the Q-factor is about 20,000. This makes the ratio ωt/ωr−=1.02 and the Q-factors of both modes are expected to be less than ten.

Measuring the spoiled HTS mode using a VNA, a Q-factor of about seven was obtained. However, steady state measurement Q-factor by the VNA does not tell the complete story as the Q-spoiling duration is usually quite short and the Q-spoiling circuit itself can introduce transients. To test the effectiveness of the Q-spoil system, an HTS resonator was placed in the fixed mount of the probe fixture and a separate loop used to power-match a transmitter to the resonator when it was unspoiled. In this configuration, the HTS resonator's resonant frequency is 4.346 MHz and its Q-factor is about 20,000. A 25 W, 300 microsecond pulse was then applied at the resonant frequency and the natural response following the pulse was detected, with the result shown in the upper graph of FIG. 11.

Figure 11:
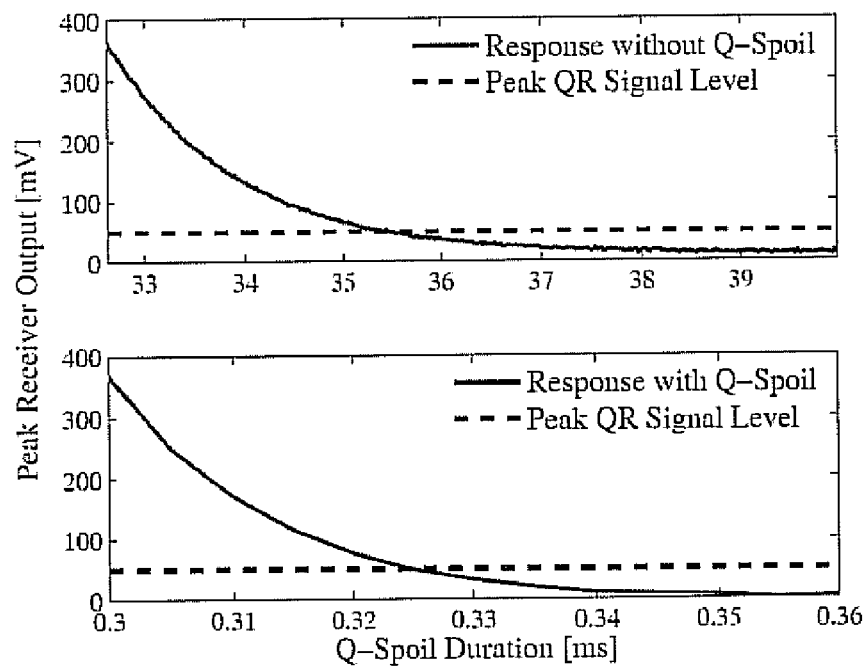
FIG. 11 shows probe natural response without and with Q-spoiling.

The lower graph of FIG. 11 shows the peak amplitude of the probe response following the Q-spoil time. By Q-spoiling the probe, the decay time was reduced by a factor of more than two orders of magnitude. A three orders of magnitude reduction was expected, and the discrepancy may arise from the transient behavior of the Q-spoil circuit, which the above analysis does not tale into account, and the transient currents generated by switching the diodes off, which provide some additional excitation to HTS resonator.

Coupling the HTS Probe to the Detection System

In both tuning and Q-spoiling the HTS probe, there was no direct electrical contact with the HTS resonator. Although HTS materials can be interfaced directly with normal metals, these interfaces introduce significant losses both through their own intrinsic resistance and through shielding current losses. Rather than making a direct electrical connection, there is an interaction with the HTS resonator's electromagnetic field. Interaction primarily through the electric field is possible, though the resonator used in this example stored the majority of the electric field energy in the resonator substrate. Other resonator designs may give larger permittivity tuning ranges. The HTS resonator was designed as a magnetic probe, and was more suitable for magnetic coupling. Both tuning and Q-spoiling were possible using magnetic coupling to interact with the resonator. The probe can also be coupled to the detection system using magnetic coupling.

Figure 12:
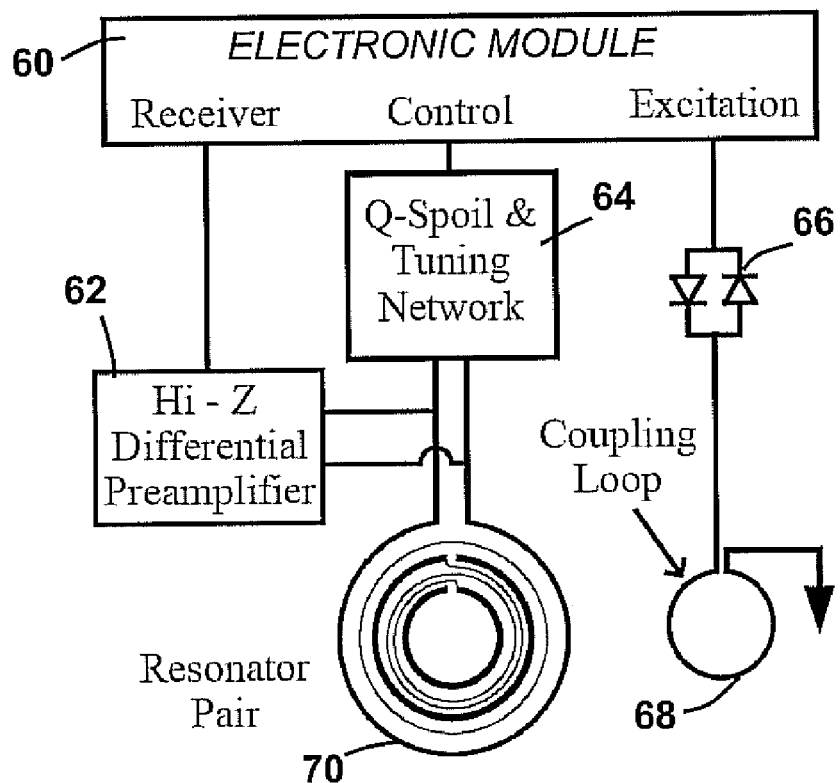
FIG. 12 shows a receiver connected to an HTS probe using a control loop.

FIG. 12 shows a schematic of an apparatus according to an embodiment of the present invention. The apparatus comprises QR detector electronic module 60, which provides excitation signals through the transmitter diode pair 66 to coupling loop 68. The electronic module provides control signals to a Q-spoil and tuning circuit 64, for example as discussed above in relation to FIG. 9. A high-impedance differential amplifier 62 is used to detect the received signal from the resonator pair 70. In this example, the resonator pair comprises and HTS resonator encircled by a control loop, for example as discussed above in relation to FIGS. 6, 7 and 9. The electronic module may comprise timing circuits, for example so that the Q-spoiling is implemented after excitation of the sample volume, and before detection of the receiver signal.

The transmitter diodes 66 form a passive switch that disconnects the transmitter from the excitation coil during receive mode. This decouples the 50 ohm transmitter impedance from the probe 70 to avoid reduction of the Q-factor, and also decouples noise from the transmitter. An experimental configuration used an ENI Model 240L amplifier to generate 25 W pulses, with the attenuator set to 13 dB. A Lark bandpass filter was used at the receiver IF output.

In an experimental implementation, the receiver pre-amplifier 62 was connected to the leads of the inner loop of the control loop. The HTS probe is greatly over-coupled by the control loop and, to avoid significantly lowering the probe's Q-factor, a high input impedance, low noise, RF pre-amplifier was used, in this example an AD8129 Hi-Z differential preamplifier.

For experiments conducted under laboratory conditions, directly connecting the pre-amplifier to the control loop provides adequate SNR for many purposes while providing a broad-band connection. By the addition of an impedance matching network between the control loop and the pre-amplifier, a lower input impedance pre-amplifier could also be used in this configuration. Further, noise matching of the amplifier may also be accomplished in the same manner. However, for the matched pre-amplifier to present a sufficiently high impedance through the noise match network, its input impedance magnitude is preferably equal to or greater than its noise match resistance.

The electronic module can be used to control the excitation of the sample volume, resonance frequency and/or Q-factor control of the superconducting resonator, to determine if a signal corresponds to a QR response, select frequency steps to maximize QR response (for example using an adaptive algorithm to speed up peak detection, and other functions. The electronic module may also control coarse tuning of a superconducting resonator, for example using a micro-drive to control the relative offset between a superconducting resonator and a dielectric wafer or other tuning element.

Figure 13:
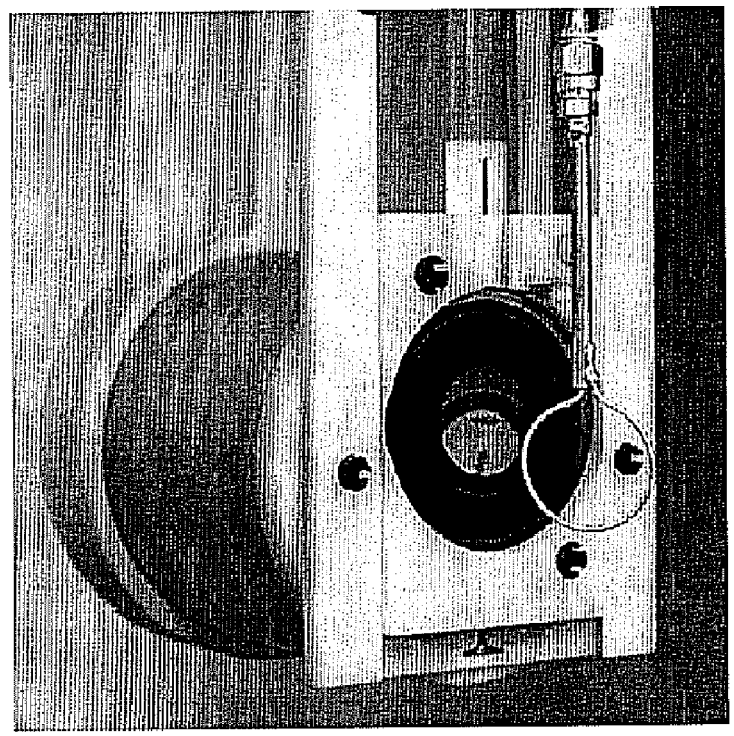
FIG. 13 shows a photograph of an HTS probe along with the sample holder
Figure 14:
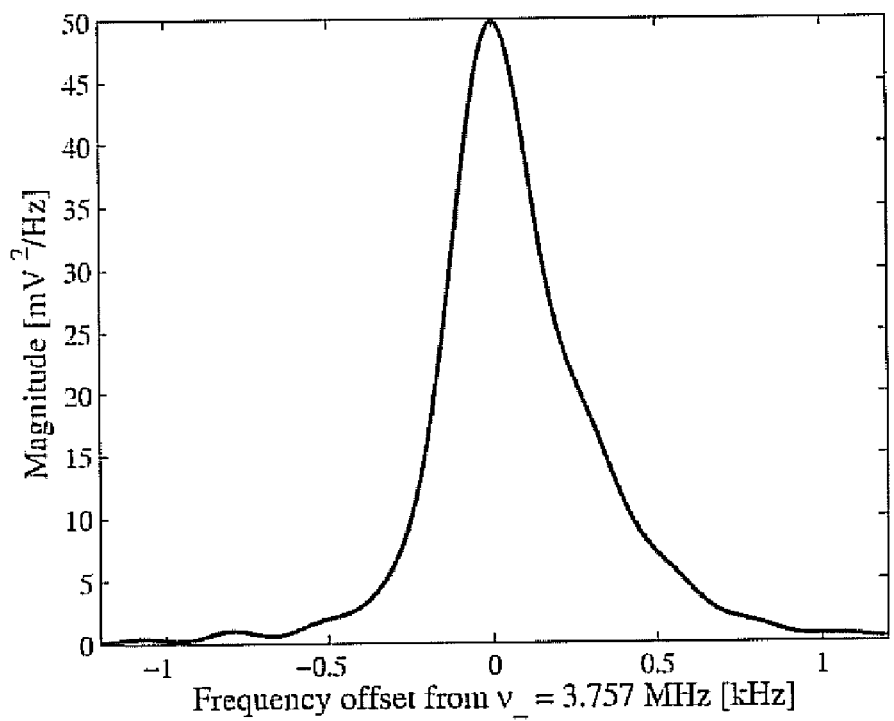
FIG. 14 shows an ESD spectrum of an analyte.

Initial tests to validate the basic function of an HTS probe, using an apparatus configured as shown in FIG. 12, used a sodium nitrite sample. A photograph of the probe is shown in FIG. 13. The ν− line-width and spin-spin relaxation time constants are similar to the RDX ν− at 3.4135 MHz. Additionally, it is quite safe to handle, readily available, and has a sizable QR response. The probe was tuned to the 3.757 MHz transition of sodium nitrite at 77 K. The sample container held about 400 g of sodium nitrite. In this experimental configuration, the Q-factor of the probe in the receive state is approximately 11,000 as measured by a NWA using loosely coupled excitation and reception coils. The probe's low Q-factor is attributable to shielding current losses incurred by the proximity of the coupling loop to the HTS resonator; the coupling loop was moved especially close to allow power matching during the excitation pulse.

An initial validation test obtained a free induction decay (FID) from the sample. An excitation pulse power of 25 W was applied for 200 microseconds and the resulting FID obtained. The FID shows evidence of the HTS resonator impact on the measured response in that the response initially grows in amplitude as the probe rings up the QR response. The FID's spectral line has a FWHM line-width of 344 Hz rather than the expected 600 Hz for sodium nitrite. The line-width corresponds directly to the measured bandwidth of the HTS QR probe.

A spin echo signal was also obtained, which cannot be mistaken for the probe's natural response. A basic spin echo comprises applying an excitation pulse followed a brief time, called the time to echo, $T_E$, later by a rephasing excitation pulse. Both pulses are followed by the expected FIDs, however, after the second pulse, a spin echo occurs with a peak at $T_E$ following the second pulse.

Figure 15:
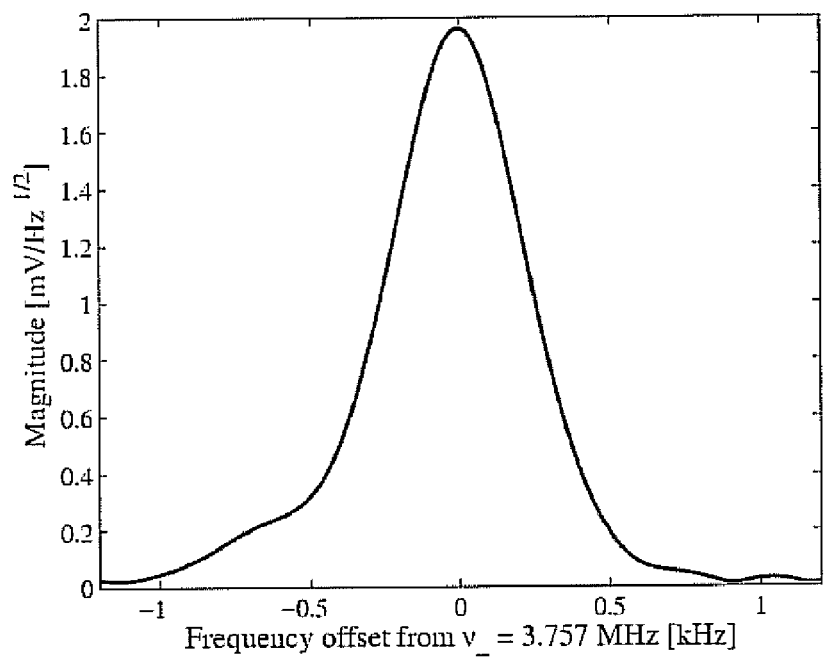
FIG. 15 shows a spin-echo spectrum of an analyte.

Both pulses used an excitation pulse power of 25 W and both were 200 μs in duration. The time to echo was chosen as $T_E$=10 ms to keep the second FID and the spin echo from overlapping in the receive window. The spin echo spectrum is shown in FIG. 15. The leading and trailing edges of the echo have slightly different time constants, as the leading edge is due to the rate the QR signal rings up the probe while the trailing edge is due to the rate which the probe itself rings down. The center of the echo is also displaced slightly due to the probe's group delay. The spectrum has a FWHIVI of 366 Hz again corresponding to the HTS QR probes bandwidth rather than the line-width of the sodium nitrite sample.

The QR probe is used to transduce the QR magnetic induction signal into a signal voltage for the receiver. In general, the probe is also a tuned circuit and acts as a band-pass filter. When a conventional probe has its pass band centered on the transition frequency, the QR signal is largely unaltered by the probe's response as the probe's bandwidth is one to two orders of magnitude larger than the QR linewidth. However, when the HTS probe has its pass band centered on the transition frequency, the QR signal can be significantly filtered by the probe as its bandwidth is on the same order as the transition line-width. For example, the HTS QR probe as configured for the experiments above had a bandwidth that is about one half that of the sodium nitrite transition. Both the FID and the spin echo show some spectral reshaping by the probe. For QR spectroscopy, spectral reshaping would require compensation. However, for contraband detection systems, the spectrographic information regarding the sample is known, and objective is to determine if contraband is present or absent.

Figure 16:
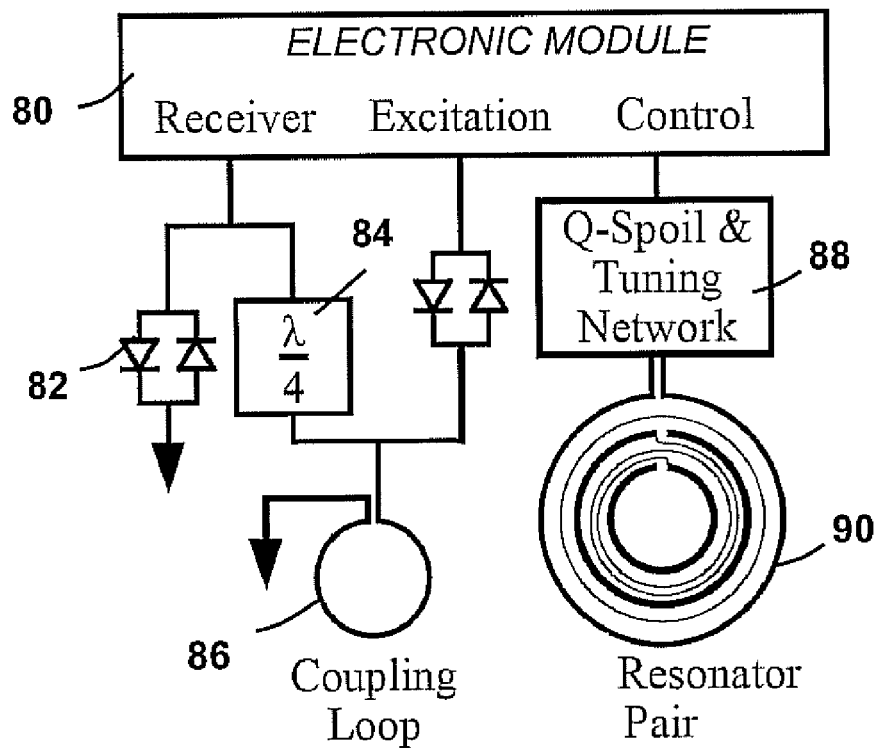
FIG. 16 shows a receiver duplexed to an HTS probe using a duplex loop.

FIG. 16 shows an alternate configuration, introducing a second coupling loop and connecting the amplifier to this loop. The receiver duplexed to HTS probe using the duplex loop. The schematic shows a QR detector electronic module 70, diode pair 82, phase shifter 827 coupling loop 86, Q-spoil and tuning network 88, and resonator pair (comprising an HTS resonator and a control loop) at 90. The coupling loop geometry and its location can be altered to provide a wide range of matching conditions. In effect, it serves as a matching network between the pre-amplifier and the HTS probe. However, geometric matching is also frequency dependent and needs to be tuned in concert with the probe.

With the addition of a duplexer, this loop can also be used to couple the excitation power amplifier to the HTS probe. As shown in FIG. 16, the pre-amplifier is incorporated in the receiver. When configured with two coupling coils, the control loop and the duplexer loop, the HTS probe may be used as a direct replacement for conventional solenoid probes in a research spectrometer.

The HTS probe may not be reciprocal between excitation and reception. The probe Q-factor is impacted by excitation power and this in turn directly changes coupling between the probe and the coupling loop. If the probe is coupled to produce a 50Ω noise match for the pre-amplifier, during excitation the probe under-couples the power match. If the probe is coupled to produce a 50Ω power match for the power amplifier, the probe over-couples the noise match. Both conditions can not be achieved without the addition of an additional matching network. When using the probe in this configuration, the probe may be noise matched, and the consequence of a poor standing wave ratio accepted. When using a separate excitation probe, this problem may be eliminated.

AN HTS probe may not provide sufficient excitation to for a large search volume as required by contraband detection. Using a separate conventional probe to excite a search volume, the HTS probe can be optimized for reception only, free from the additional constraints imposed on a probe serving both roles.

QR Response Detection

A QR response was detected from the explosive RDX using the multi-pulse sequence CPMG. For this validation test, the HTS probe was configured to duplex excitation and receiving as shown in FIG. 16. The duplex loop was configured to noise match a 50Ω low noise pre-amplifier. In this configuration, the Q-factor of the probe in the receive state is approximately 19,000 as measured by a NWA using loosely coupled excitation 110 and reception coils. The improvement in Q-factor is due to the fact that the duplex loop can be positioned much further from the HTS resonator when noise matching rather than power matching.

The multi-pulse sequence CPMG (a π/2 pulse followed by a series of π rephasing pulses) was calibrated by measuring the amplitude of the FID as a function of pulse width. A 400 g sodium nitrite sample was used, and the probe was tuned to the 3.757 MHz transition of sodium nitrite at 77 K. Using a 25 W pulse power, the pulse width was varied from 50 µs to 550 µs in 50 µs steps. The resulting data was fitted to a first order spherical Bessel function, showing that the π/2 pulse is 305 µs and the 7π rephasing pulse is 566 µs.

An experiment to detect RDX was performed. RDX has three sets of transition frequencies, due to three non-equivalent nitrogens connected to its triazine ring, and the probe was tuned to the 3.4135 MHz transition of RDX at 77° K. The sample used was the non-explosive equivalent NESTT-RDX. There was approximately 23 g RDX in the sample container. As the sample weight of RDX is much less that the sodium nitrite sample and only one of the six 14N atoms in RDX produces the 3.4135 MHz transition, the expected signal amplitude is much lower than that available from the sodium nitrite sample. To compensate for the reduced SNR, 50 echoes were acquired from the CPMG sequence using a time to echo of 5 ms and repeated the sequence 4000 times. A composite spin echo was produced by averaging all 200,000 echoes produced by the experiment.

Figure 17:
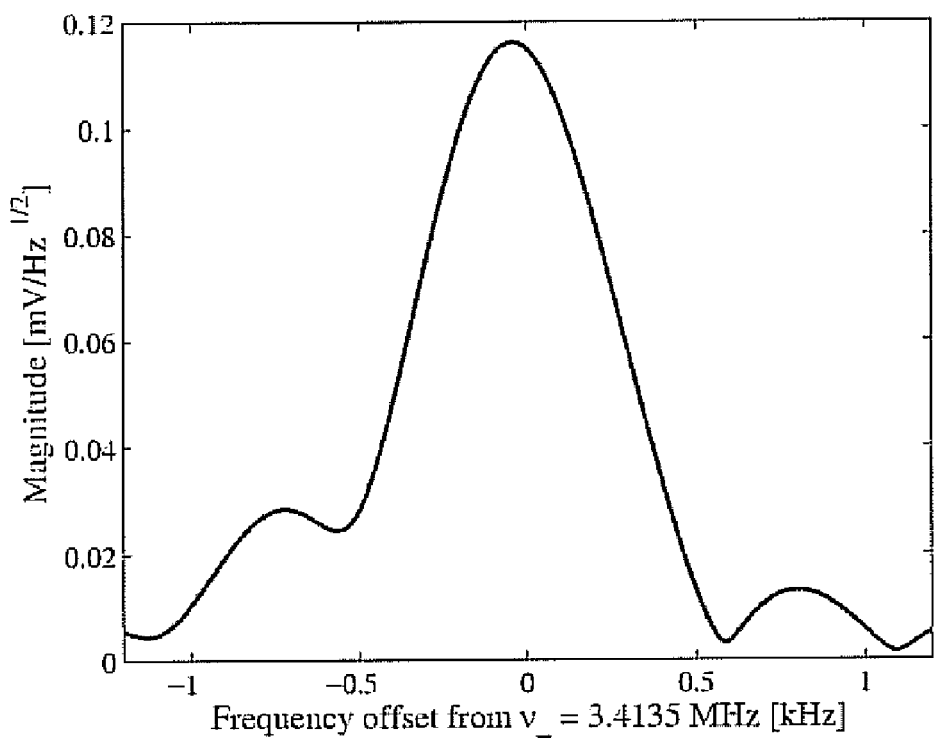
FIG. 17 shows an RDX spin-echo spectrum of an analyte.

FIG. 17 shows the spin-echo spectrum of the RDX equivalent. The spectrum is appreciably broadened due to the brief duration of the data acquisition window of 2.464 ms. The spectrum of the window function has a FW bandwidth of 490 Hz and when the window's spectrum is convolved with the spin echo spectrum the resulting FWHM bandwidth is 660 Hz. This means that the spin echo spectrum itself would have a FWHM bandwidth of 170 Hz, placing the probe's Q-factor at 20,000. Hence, using a spin-echo detection scheme, it was possible to excite and detect a QR resonance using a single HTS resonator.

Detection Algorithms

Detection may be accomplished by tuning the probe to various frequencies and estimating parameters of the QR lineshape from measurements at these frequencies. The actual detection may then be based on the parameter estimates and the error between the actual measurements and data. Algorithms used may differ in how they command the system to tune the probe. In representative examples, a blind search algorithm tunes the probe cover a frequency span in uniform sequential steps. In other approaches, the largest signal is located by tuning to the estimated location of the transition frequency based on earlier measurements, and subsequent frequencies chosen that improves the parameter estimates.

A search algorithm (which may also be called an adaptive algorithm) may be evaluated by performing a series of detection experiments, for example by evaluating its ability to boost signal strength, provide accurate estimates of the lineshape parameters, and provide good detection performance. Detection performance may be evaluated by means of receiver operating characteristic (ROC) curves. An adaptive search algorithm may not give good estimates of the lineshape parameters, but was able to obtain ROC performance comparable to a blind search algorithm in half of the detection time of the blind algorithm.

The HTS QR probe frequency control can use an adaptive algorithm to optimized the probability of correct detection and minimize the probability of false alarm, per unit time. For example, An HTS QR probe allows coherent addition of the QR response obtained using either the SORC or PAPs-NPAPs sequence when the temperature of the analyte (such as an explosive) is unknown. In comparison to normal metal probes, using these techniques in conjunction with a QR HTS probe increased the SNR per unit time by more than 20 dB. Feedback control algorithms may also be used that automatically compensate for any temperature uncertainty of the analyte. Algorithms may also be adapted to adjust the HTS QR probe frequency, and provide temperature-independent SORC and PAPs-NPAPs pulse sequences.

An adaptive algorithm was used for tuning the HTS QR probe that resulted in higher detection performance per unit time than a blind search for a QR transition by systematically moving the HTS QR probe frequency across the spectral range of interest.

Various search algorithms may be used to locate the QR response of an analyte. An example blind search may use equal search frequency steps across an entire expected frequency range. Other possible adaptive algorithms include Maximization of Energy from Single Signals (MESS), where a new probe frequency is found from an estimated QR transition frequency determined from measurements made at previous probe frequencies, and Minimization of Energy Estimate Covariance (MEEC), where a new probe frequency is chosen to minimize LS covariance. An adaptive algorithm may be used to shorten detection times, relative to a blind algorithm. A MEEC algorithm can be used to improve parameter estimates of the QR response.

Blind Search

In an example blind search algorithm, the frequency spacing $d = (f_{max} - f_{min})/N$ where N is the number of frequencies available, and the first frequency is $f1 = f_{min} + d/2$. The minimum search spacing may be influenced by signal-to-noise and other parameters. For example, the following relationship may be used:

$$N = \frac{f_{max} - f_{min}}{\Delta f} = (f_{max} - f_{min})\frac{N_a}{B}\left[\left(\frac{SNR_0}{s-1}\right)^{\frac{1}{2}}\right] \quad (4)$$

where $f_{min}$ is the minimum frequency, $f_{max}$ is the maximum frequency, $N_a$ is the number of points required above the noise floor ratio, B is the energy Lorentzian bandwidth parameter, and $SNR_0$ is the maximum available S/N at the transition frequency.

Here, the number of search points N is proportional to the frequency span to be covered and the number of frequencies required above the noise, and inversely proportional to the sum of the bandwidths of the QR line and the probe. As an example, consider covering a span of 16 kHz using a probe bandwidth of 250 Hz to find a QR transition with a FWHM of 750 Hz. If the maximum SNR is 3 dB through averaging and at least 3 measurements 1.5 dB above the noise floor are desired, then at least 30 measurements spaced about 530 Hz apart are needed.

A SLSE type pulse sequence was used, with a pulse spacing of $\tau=6$ msec. The pulse spacing was chosen in light of the $T_2$ time constant (which determines the amplitude of signals as a function of pulse spacing) for the analyte, and the fact that the narrowband HTS probe has a very long time constant and hence the spin echo persists for a longer period of time than it would with a wider bandwidth probe. Additionally, by choosing a sufficiently long $\tau$, the FIDs from the rephasing pulses do not interfere with the spin echoes. The pulse width was chosen to artificially reduce the signal size by reducing the pulse width and hence the amount of nutation of the nuclei. A pulse width of 42 μsec was chosen, to obtain SNR of about 3 to 5 dB. The first two echoes are averaged and one phase-cycle was performed. The SNIP. was approximated by $$SNR \approx 10\log_{10}\left(\frac{E_{signal} - E_{noise}}{E_{noise}}\right) \quad (5)$$

where $E_{signal}$ is the computed energy of the signal and $E_{noise}$ is the energy of the noise approximated by averaging energy calculations over several signals obtained by exciting at some frequency sufficiently far from the transition frequency that no QR signal was present.

In an example blind search experiment, the probe was tuned so that when the D7 (D=64) bit was enabled (the center of the tuning range), the center frequency was at 3.757 MHz. Blind data points were taken starting at a value of D=4 and ending at a value of D=124 spaced evenly over 20 points. To obtain results for 10 data points, every other data point from the 20 data point set was used.

Adaptive Search

One example is a maximization of energy from signals search (MESS). At least 3 points are needed to produce an initial estimate of the transition frequency using a least squares (LS) estimate based on signal energy versus probe frequency. A certain number $N_i$ of initial frequencies may be chosen in a manner similar to that of a blind search. Poor estimates for the bandwidth parameter are possible. For example, if a perfect estimate of the transition frequency is obtained using the $N_i$ initial points, the algorithm then places further points at the peak, and the error in the estimate of the bandwidth does not improve beyond that of the initial estimate.

Another approach is a Minimization of Energy Estimate Covariance (MEEC) Algorithm, a closed-loop algorithm that bases computation of the probe frequency $f_k$ on an estimate of the QR transition properties. The algorithm attempts to minimize the covariance of the least-squares estimates of the lineshape parameters. After several measurements, the next frequency may be calculated as $$f_k = \max\{\arg\max_f |\Phi^T W \Phi|(f)\} \quad (6)$$

the frequency corresponding to the largest calculated predicted value of $|\Phi^T W \Phi|$ where the matrix F comprises regressor vectors and W is a positive defining weighting matrix. Here, max { . . . } is used to account for possible multiple or nonexistent peaks. The calculation is performed numerically for a large number of frequencies. It is possible that this approach misses the actual peak frequency, but for the parameter values used the function is fairly smooth and the peak can generally be easily identified.

If the temperature of the sample is non-uniform, a single Lorentzian may not well describe the lineshape. The method may be adapted using a multi-Lorentzian or other curve fitting algorithm.

A further approach uses Enhancement of Algorithms via Single-Signal Estimates (EASSE). When the SNR is sufficiently large, information about the QR lineshape can be recovered from the individual signals. Parameters may be obtained by dividing the signal ESD by the estimated probe ESD and fitting the result to a squared Lorentzian shape. There are two estimates of the lineshape parameters available: the estimates from the signal and the estimates from the signal energy versus probe frequency fit. The single signal may provide a good estimate, but the signal energy versus probe frequency estimate may also be used as it may be less prone to a single burst of noise. The two estimates may be combined in a weighted average. The energy estimates may be weighted by the sum of previous energies and the current signal estimate by the energy of the current signal. As more signals are taken, the sum of energies increases and the energy estimates are weighted more. However, if a single signal with large SNR (and hence large energy) is encountered, it can be given an appropriately large weight in the average. The weighting of the two estimates may be even, or one weighted by zero, for example if one estimate is unreliable.

Hybrid search algorithms may also be used, such as a hybrid of the MESS and MEEC algorithms. In a representative example, the algorithm is initiated with a blind spiraling search until a signal is observed with an ESD peak above the signal threshold. Once this occurs, the MESS algorithm is used to find the frequency to maximize the signal energy. This is iterated a specified number of times, accumulating energy data points near the transition frequency (if the signal is, indeed, a QR signal). With more points accumulated near the QR transition, the LS algorithm is more likely to estimate the transition frequency correctly.

Once a sufficient number of signals are observed, the MEEC algorithm can be used to improve the LS estimate by intelligently interrogating frequencies away from the transition frequency. The algorithm may be structured so that it escapes the MESS portion of the algorithm if the signal level is not consistently above the threshold, so as to improve the rejection of spurious bursts of noise.

In an example adaptive search experiment, an energy maximizing (MESS) algorithm was used. The energy fit estimates were poor, and the single signal estimates (EASSE) were used for peak searching. The MESS algorithm was nested in a blind search algorithm to avoid getting stuck at a burst of noise. The blind portion of the search was started at a value of D=43 spiraling out with steps of 12. This gives the search algorithm about the same chance of "finding" a signal since it gets as close to the transition frequency as a blind search does. A test search was started away from the transition frequency to simulate the fact that in a realistic detection system the transition frequency may not be known.

Figure 18A:
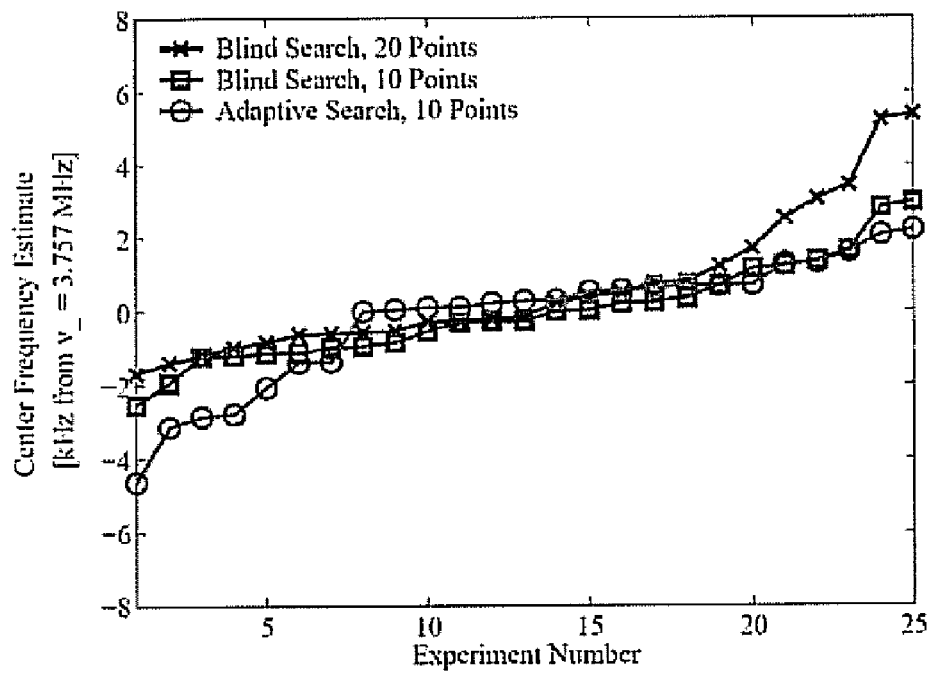
FIGS. 18A and 18B show data obtained using probe tuning algorithms.

FIG. 18A shows the results of the transition frequency estimates for the blind search algorithm (for 10 and 20 points) and the MESS algorithm. The adaptive algorithm tends to estimate the transition frequency closer to the actual frequency 3.757 MHz for the sodium nitrite sample used, though there are some outliers. The data is sorted for clarity and the experiment number does not necessarily imply order or correlation between experiments.

Figure 18B:
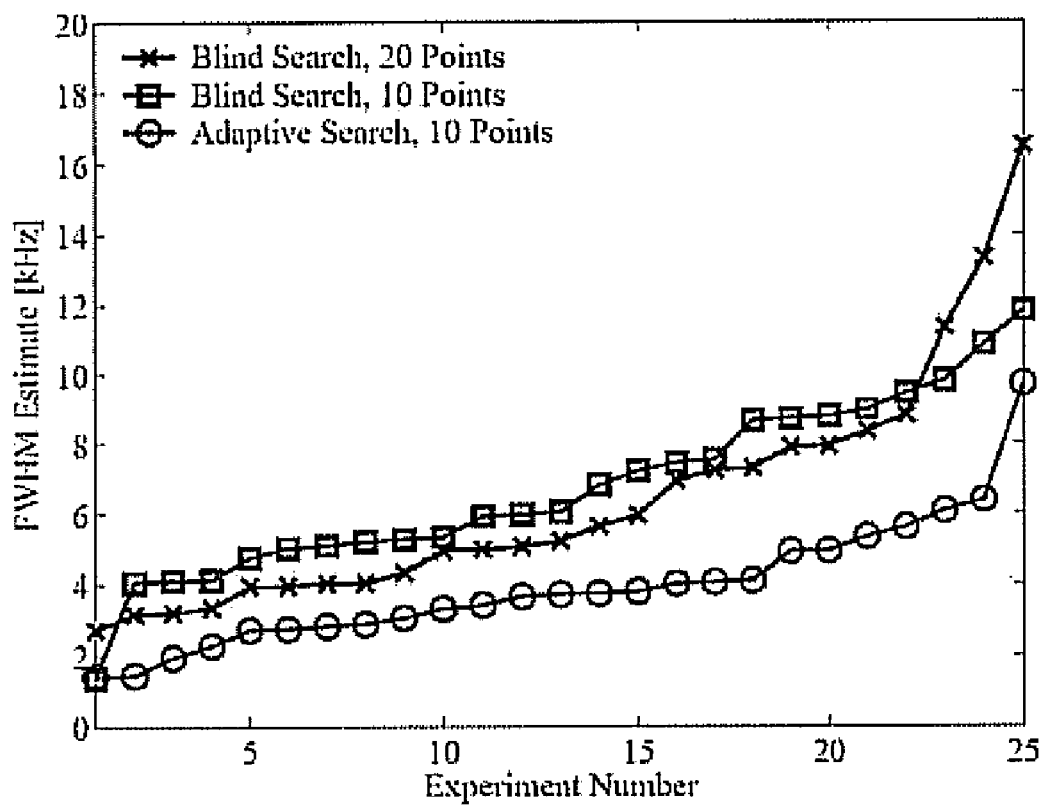

FIG. 18B shows the results of the FWHM estimates for the same data. Almost all of the estimates were high, as the expected FWHM was around 1-1.5 kHz for a 750 Hz–1 kHz QR line and a 200-300 Hz probe, though the adaptive search tends to estimate a lower FWHM and hence was closer to the true value.

Using the signal energy, the adaptive MESS algorithm was capable of performance superior to the blind search algorithm. The MESS algorithm obtained comparable performance to the blind search algorithm in about half the time.

Other Aspects of Data Collection

Searching for a QR response across a range of frequencies reduces the overall SNR per unit time. For example, increasing the Q-factor by a factor of 100 would imply a 20 dB improvement in SNR. However, because the bandwidth of the QR probe is reduced by a factor of 100, more measurements are needed in order to locate the QR response in frequency, hence reducing the overall SNR per unit time by increasing the acquisition time.

In embodiments of the present invention, the Q-factor of a quadrupole resonance (QR) probe is raised by orders of magnitude using a high temperature superconducting (HTS) resonator. This approach trades improved signal-to-noise ratio for reduced detection bandwidth. When combined with a potentially strong temperature dependence of the transition frequency, the signal may need to be searched over a wide frequency range. However, by deriving spectral representations of the QR signals and expressions for the strength of the response as a function of the probe's frequency relative to the transition frequency, a search algorithms can be used for detecting QR signals when the probe bandwidth is on the order of, or less than, the QR linewidth of the analyte.

False alarm rates for QR detection may be also reduced by characterization of the analyte lineshape. A combination of algorithms, or hybrid algorithm, can be used to improve data fitting and lineshape analysis. Fuzzy logic heuristics may be used to determine QR parameters, with weights given to amplitude, linewidth, and frequency location. Detection based on fitting the signal energy to a simple Lorentzian shape may be hindered by the poor SNR of the signal energy measurement, temperature distributions, and the simplicity of the estimation algorithm used. Hence, other fitting approaches may be useful.

Pulse sequences which may be used include strong off-resonant comb sequence (SORC), and spin-echo pulse sequences such as spin-lock spin echo (SLSE), and Carr-Purcell-Meiboom-Gill (CPMG). Data was obtained from frequency domain data using a FFT engine, though time-domain algorithms such as multiple signal classification (MUSIC) and estimation of signal parameters via rotation invariance techniques (ESPRIT) may also be used. ESPRIT can be used to obtain a direct estimate of frequency. An ESPRIT algorithm may obtain estimates where there is very low SNR, which is useful for locating the transition when the probe frequency is far away from the actual transition frequency.

The observed frequency of the QR response generated by either the SORC or PAPs-NPAPs sequences using a narrow-band QR probe may be determined in part by the center frequency of the QR probe, and this information can be used to eliminate the dependence of the QR response generated by these sequences on the temperature of the analyte.

A simple least-squares estimate can be used to obtain estimates of the center frequency and bandwidth from a set of frequencies $f_k$ and energy measurements $E_k$. The following relationship may be used:

$$\sqrt{E_k - \hat{\sigma}^2} \approx \frac{A}{1 + 4\left(\frac{f_k - v_m}{B}\right)^2} \quad (7)$$

Here, $f_k$ and $E_k$ are the probe frequency and energy for the kth experiment, and A is amplitude. The term in σ is a noise variance term that may be determined from multiple samples, as the expected value of energy is equal to the sum of the signal energy and the variance of the noise $\sigma^2$. The QR transition frequency is automatically acquired, and $T^*_2$ can be calculated by estimating the probe bandwidth using a ping experiment. At least three measurements are required to obtain a least squares fit. The benefit of such a multiple experiment energy fitting method is the effective averaging of the results of several experiments, rather, than relying upon only the current signal. This helps reduce the effect of noise bursts. The SORC pulse sequence destroys the QR bandwidth information by windowing the signal in time, so that the energy fitting method allows recovery of the QR bandwidth using the signal energy over several experiments.

The energy spectral density of a QR signal received by a narrow band probe can be approximated by the product of two Lorentzian shapes, one located at the probe center frequency with the probe's FWHM and one located at the QR transition frequency with the QR FWHM.

The energy of a signal received with a probe tuned away from the transition frequency by Δf approximately follows a Lorentzian shape centered at FE Δf=0 and with a FWHM given approximately by the sum of the QR and probe FWHMs.

A Lorentzian lineshape description may only be valid for QR samples of uniform temperature. As analytes may be distributed across a large volume, a significant temperature gradient may exist. In this case, the lineshape is not a Lorentzian, or even symmetrical about a nominal v*. A more general lineshape for curve fitting may be used.

A possible method for improving SNR is to use a signal metric such as the peak value of the ESD within a certain range of the probe frequency. An adaptive algorithm can reduce false alarm rates through better characterization of the QR lineshape, particularly if the fit quality can be improved. An ESPRIT algorithm may be used for obtaining frequency estimates from the QR signals.

Q-Factors Measured Using a Noise Spectrum

To obtain Q-factor measurements at the lower excitation levels comparable to QR responses, a noise excitation measurement method was developed. This method determination of the Q-factor at an excitation level six orders of magnitude lower than conventional techniques.

Figure 19:
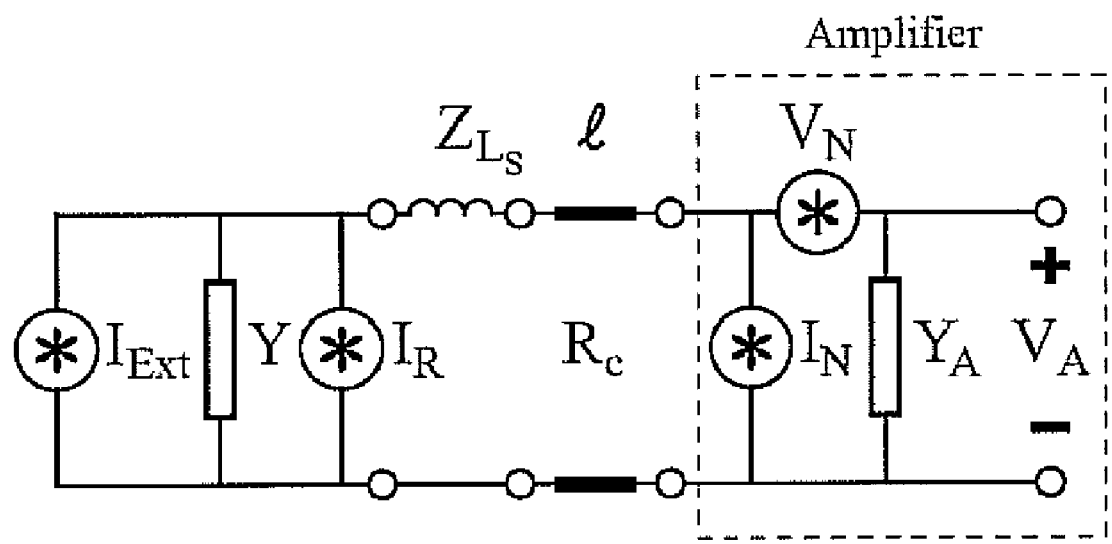
FIG. 19 shows an equivalent circuit for a noise excitation Q-factor measurement.

An HTS resonator was connected to a spectrum analyzer through an amplifier. The spectrum analyzer then measures the resulting noise power spectrum. The equivalent circuit for the noise excitation measurement is shown in FIG. 19, where $V_A$ is voltage input to the amplifier, $Y_A$ is the admittance of the amplifier, Y is the admittance of the HTS resonator, and $Z_{LS}$ is the impedance of the coupling inductor. It is assumed that only the resonator admittance varies significantly with frequency over the bandwidth of interest. An additional noise source, $I_{EXT}$, is added to account for the noise injected into the system. The connection between the amplifier and the spectrum analyzer is not modeled here as it simply adds a constant scale factor to the noise power spectrum.

Because the circuit in FIG. 19 contains a transmission line (with a small phase angle), analysis of the system is more easily accomplished using a signal flow graph rather than circuit analysis. See J. K. Hunton, "Analysis of microwave measurement techniques by means of signal flow graphs", IRE Transactions on Microwave Theory and Techniques, 6(2):206-212, 1960.

The power spectral density of the amplifier input is approximated by:

$$|V_A(\omega)|^2 \approx \left|\frac{I_T}{Y(\omega)}\right|^2 + |V_N|^2 \quad (8)$$

This is a Lorentzian, due to the term depending on the magnitude squared of the resonator admittance, plus a constant offset, due to the amplifier's voltage noise. Here, $I_T = \sqrt{I_{Ext}^2 + I_R^2 + I_N^2}$, and this equation assumes the admittance of the amplifier is small compared with the resonator admittance at resonance. A Q-factor of approximately 700,000 was determined for an HTS resonator using Lorentzian fitting.

Cloaking

In further examples of the present invention, a SLR (shielded-loop resonator) or other excitation coil may be used for excitation, and an HTS probe used for detection. The HTS probe is susceptible to damage from high energy pulses. The term "cloaking" refers various approaches to reduce energy dissipated in the HTS probe by the excitation pulse, including detuning the HTS probe during an excitation pulse, and operating the HTS probe in a null of the excitation coil response.

A diode-based switching circuit may be used. HTS probes are expensive, and easily destroyed by large fields from the exciter coil. Operating the HTS probe in a null protects the probe from damage, and improves reliability. Normal metal detector coils, such as copper, may be warmed but typically not destroyed by large fields from the exciter coil. In the case of conventional receiver coils, there is benefit to being near a null, but it is not so important to be operating exactly at the null.

HTS diameters of 2-6 inch diameters were evaluated, and the larger diameter probes were found to detune the SLR. Various approaches can be used for cloaking, including semiconductor device tuning, switched capacitors and the like. A switched capacitor can be used to move excitation and/or receiver frequencies, for example providing a null located at the excitation frequency.

In an example system, a quasi-Helmolz pair shielded loop resonator was used, with a 60 cm spacing between the coils. RF power was fed through a matching capacitance to a center conductor of a coaxial cable, which acts a primary of a transformer. The secondary is the outer shield, which is resonated by a resonating capacitance. The ground path for the resonating capacitance is interrupted by a "cloaking" FET. When the FET is on, the circuit resonates at the desired transmit frequency ("uncloaked"). When the FET is off, the resonant frequency moves well above the QR frequency ("cloaked"), protecting the sensor from transmitted radiation. Power dissipation in the HTS probe was reduced by a factor of 10, or greater. This has advantages for signal detection, and SNR.

Cloaking can be combined with Q-spoiling, for example using a copper control loop having a resistor switched into the circuit. The natural modes of two resonators with the same frequency is a function of coupling. A higher frequency and lower frequency mode can be achieved, with a null between them. For a given coupling, the splitting is maximized when the natural frequencies are identical. The interaction between separate transmit and sensor coils can be used to cloak both the transmit and sensor coils from each other. Switched capacitors, for example using semiconductor switching, can be used to hide an HTS sensor resonator from an SLR (or other) transmitter coil.

Cloaking an HTS Probe from a Tuned Normal Metal Excitation Probe

In an example mode of operation, a QR response is excited using a low Q-factor normal metal probe and observed using a high-Q HTS (superconducting) probe. As both the excitation and receiver probes have nearly the same frequency, they electrically couple to produce two resonant peaks that are displaced from the desired excitation and receive frequencies. When cloaking the HTS probe from the excitation probe, the HTS probe does not detune the excitation probe.

In order to cloak the HTS probe during the application of an RF pulse, a sufficiently large capacitance can be connected across a control loop, so that the tuned control loop and HTS resonator produce two resonance peaks that are located outside the pass-band of the tuned excitation probe, and a null located at the excitation frequency. A control loop may be a copper loop encircling the HTS resonator, such as discussed above.

It is possible to analytically calculate the value of capacitance so that the tuned control loop and HTS resonator produces two resonant peaks that are located outside the passband of the tune excitation probe, and a null located at the excitation frequency.

Figure 20:
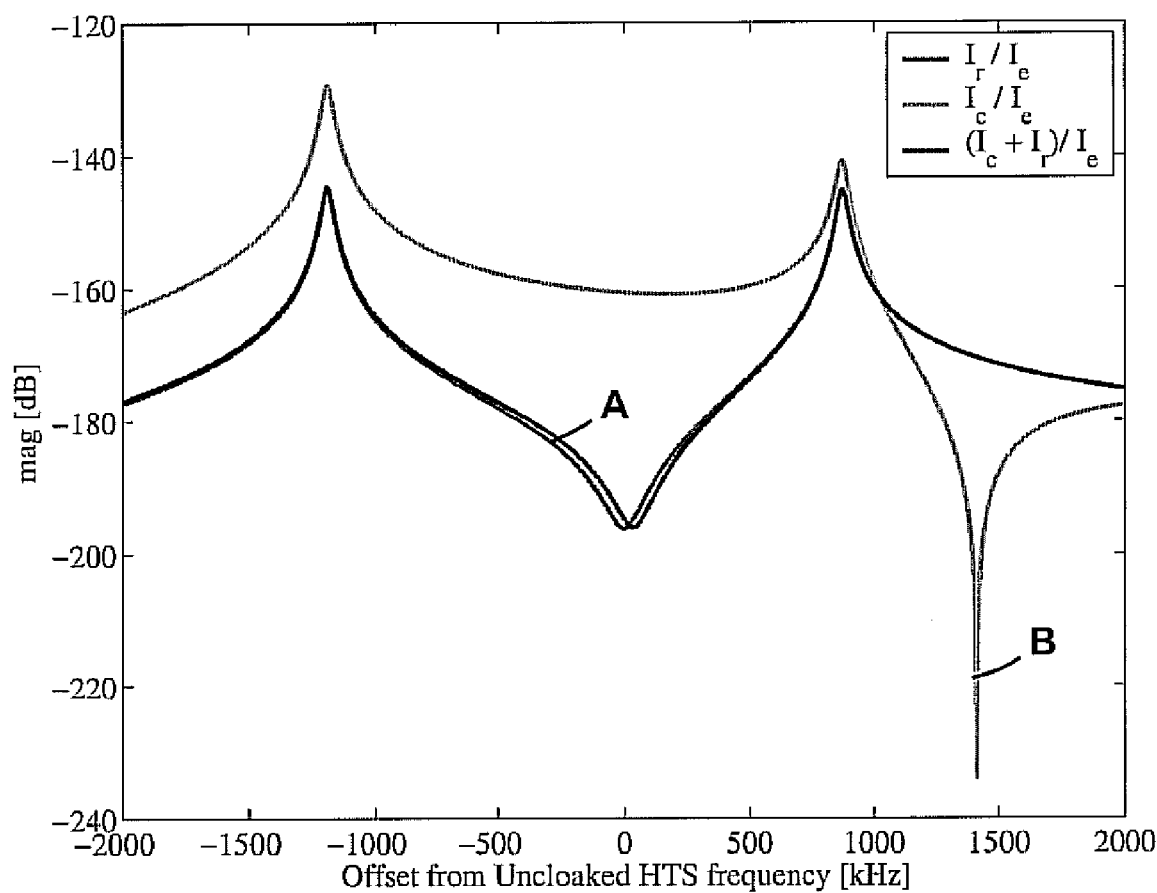
FIG. 20 shows simulated cloaking behavior.

FIG. 20 shows the simulated cloaking behavior. The horizontal axis indicates the magnitude of a transfer function in dB while the horizontal axis represents frequency with respect to the operating frequency of the HTS probe. In other words, zero Hertz maps to the frequency of the explosive. The curve 'A' shows the transfer function from the current in a copper excitation coil, $I_e$, to the induced current in the resonator, $I_r$. Through appropriate choice of the cloaking capacitance, a null (zero) was placed at the operating frequency of the resonator. This is indicated by the dip in the curve at zero Hertz. The curve 'B' shows the transfer function from the current in a copper excitation coil, $I_e$, to the induced current in the control loop, $I_c$. Note that the current is much larger in the control loop than in the HTS resonator. Because the currents in the control loop and FITS resonator are out of phase, the magnitude $I_c + I_r$ is smaller than $I_c$.

Figure 21:
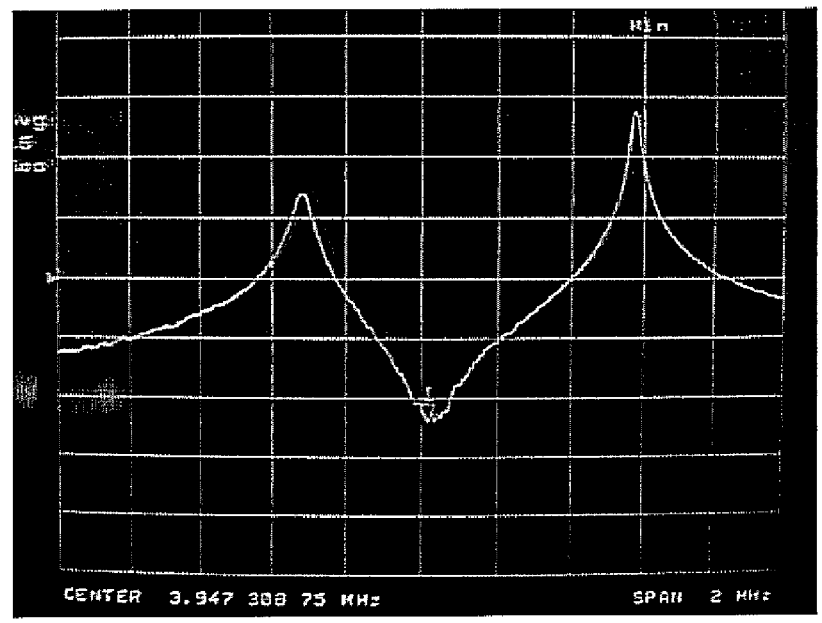
FIG. 21 shows experimental measurements made using a HTS probe with cloaking

FIG. 21 shows experimental measurements made using an HTS probe. The graph represents the magnitude of $I_c + I_r$. The external capacitance is chosen to place the null, indicated by marker 1, in the resonator current at the tuned frequency of the resonator.

Cloaking a Normal Metal Excitation Probe from an HTS Probe

During reception of the QR response by the HTS probe, the presence of the excitation probe is cloaked by electrically shifting its tuned frequency outside the pass-band of the HTS probe. Cloaking is affected by temporarily changing a capacitance in the tuned excitation probe.

Cloaking may reduce power dissipation in the detector probe, e.g. by a factor of 10 or more. The use of cloaking with a transient HTS probe has never before been demonstrated. Probes may be tuned by mechanical displacement, for example relative to another coil. In some examples, a single HTS probe can be used for both excitation and detection, for pulsed QW and for CW experiments.

Applications

Applications of QR probes according to the present invention include security (such as aviation security), scanning packages moving through subway and bus terminals, mine countermeasures, detection of improvised explosive devices, anthrax detection, medical imaging, and scanning vehicles for explosives.

Patents, patent applications, or publications mentioned in this specification are incorporated herein by reference to the same extent as if each individual document was specifically and individually indicated to be incorporated by reference.

Other Aspects

Improved probe design, signal processing, and control methods allow improved detection performance attainable with narrowband quadrupole resonance (QR) probes fabricated from thin-film high-temperature superconducting (HTS) resonators. An HTS QR probe can be used in an improved apparatus that detect analytes concealed within containers such as luggage, mail, improvised explosive devices, and minimal metal landmines.

In comparison to existing QR probes fabricated from normal (non-superconducting) probes, an HTS QR probe improves the signal-to-noise ratio per unit time, by an order of magnitude or more. Embodiments of the invention provide greater than an order of magnitude improvement in sensitivity and the ability to reject RF interference sources located outside the pass-band of the HTS QR probe.

In addition to aviation security, other applications of HTS QR probes include scanning packages moving through subway and bus terminals, mine countermeasures, detection of improvised explosive devices, and scanning vehicles for explosives. Other nuclei can be detected using QR, such as isotopes of Cl and Cu. The invention is not limited to analysis or detection of nitrogen compounds. Using a high-temperature superconducting probe to increase the Q-factor trades improved signal-to-noise ratio for a reduced detection bandwidth. However, an improved QR detection system can automatically search for a QR response using automatic tuning of the HTS QR probe. A temperature detection system, such as a thermal camera, may be used to estimate the temperature of the analyte environment, and automatically select a scanned frequency range.

A narrow bandwidth of the probe improves SNR, and is more sensitive to the relative location of the probe and transition frequencies. Hence, in order to detect a QR sample several experiments are performed with the probe tuned to different frequencies. The QR lineshape parameters can be estimated based on both the spectrum of a single signal and the energies of several signals taken at different probe frequencies. A detection system may obtain several signals and compress time-sampled data down to a few parameters and so to a detection metric. The detection system can either operate blindly by talking several measurements with a pre-determined probe frequency spacing, or adaptively by continually updating estimates of the lineshape parameters and choosing probe frequencies in order to improve some parameter such as signal energy or fit quality.

Additional signal processing algorithms can be used to expand the temperature range of a QR apparatus, and reduce electrical noise even when the frequencies of RF interference sources lie close to the QR response spectra. The false alarm rate of existing QR detection systems is adversely affected by the presence of AM broadcast signals, as the explosives PETN and TNT have QR frequencies that lie within the AM broadcast band. Hence, apparatus according to the present invention may have a greatly reduced false alarm rate for such materials.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Having, described our invention, we claim:

1. An apparatus to assist detection of an analyte within a sample volume using nuclear quadrupole resonance (QR), the analyte having a QR response at a response frequency, the apparatus comprising:
    a superconducting resonator having a resonance frequency;
    a coarse frequency control operable to adjust the resonance frequency so as to be proximate to the expected response frequency;
    a fine frequency control operable to adjust the resonance frequency over a frequency band including the expected response frequency; and
    an electronic module, operable to adjust the coarse frequency control so that the resonance frequency is close to the response frequency; and
    and further operable to adjust the fine frequency control so as to locate the response frequency within the frequency band.

2. The apparatus of claim 1, further including an excitation coil separate from the superconducting resonator:
    the electronic module including an excitation circuit operable to provide excitation pulses to the excitation coil; and
    the superconducting resonator being used as a receiver coil.

3. The apparatus of claim 1, wherein the superconducting resonator is used as both an excitation coil and a receiver coil.

4. The apparatus of claim 1, wherein the fine frequency controller adjusts the resonance frequency using uniform frequency steps across the frequency band.

5. The apparatus of claim 1, wherein the fine frequency controller adjusts the resonance frequency using an adaptive algorithm operable to select frequency steps so as to search for a maximum QR response of the analyte at the response frequency.

6. The apparatus of claim 1, wherein the adaptive algorithm is operable to select frequency steps so as to maximize QR response energy.

7. The apparatus of claim 1, the superconducting resonator has a resonance linewidth, the QR response of the analyte having a response linewidth and a response lineshape:
    the resonance linewidth being less than the response linewidth; and the lineshape of the QR response being determined from data obtained at a plurality of resonance frequencies within the frequency band.

8. The apparatus of claim 1, wherein the coarse frequency controller includes a mechanism for changing a position of the superconducting resonator relative to a dielectric element.

9. The apparatus of claim 8, wherein the coarse frequency controller is operable to adjust an offset position between the superconducting resonator and the dielectric element:

the dielectric element being a dielectric wafer.

10. The apparatus of claim 8, wherein the dielectric element comprises sapphire.

11. The apparatus of claim 8, wherein the dielectric element comprises lanthanum aluminate.

12. The apparatus of claim 1, further comprising a control loop surrounding a at least a portion of the superconducting resonator; and the control loop being used to modify the resonance frequency of the superconducting resonator during excitation of the sample volume, so as to reduce energy dissipated in the superconducting resonator.

13. The apparatus of claim 12, wherein a capacitor is electrically connected to the control loop during excitation of the sample volume so as to reduce energy dissipated in the superconducting resonator.

* * * * *

UNITED STATES PATENT AND TRADEMARK OFFICE
CERTIFICATE OF CORRECTION

PATENT NO. : 7,511,500 B2
APPLICATION NO. : 11/679378
DATED : March 31, 2009
INVENTOR(S) : Jeffrey L. Schiano et al.

It is certified that error appears in the above-identified patent and that said Letters Patent is hereby corrected as shown below:

Col. 3, line 16: replace "includes" with --include--
Col. 5, line 31: delete second occurrence of "on the"
Col. 5, line 40: delete second occurrence of "on the"
Col. 6, line 44: replace ""mieroohms" with --microohms--
Col. 7, line 6: replace "HTS OR probe" with --HTS QR probe--
Col. 7, line 48: replace "1,546." with --1.546.--
Col. 11, line 23: replace "lower that the shift" with --lower than the shift--
Col. 13, line 12: replace "$C_n 32\ 2C_{n-1}$" with --$Cn=2Cn-1$--
Col. 13, line 18: replace "C5=62" with --C5=62pF--
Col. 13, line 55: replace "found be determining" with --found to be determining--
Col. 14, line 50: replace "tale into" with --take into--
Col. 15, line 12: replace "and HTS" with --an HTS--
Col. 16, line 30: replace "FWH1V1" with --FWHM--
Col. 17, line 17: replace "excitation to for a large" with --excitation for a large--
Col. 17, line 44: replace "the $7\pi$" with --the $\pi$--
Col. 17, line 50: replace "less that the" with --less than the--
Col. 17, line 63: replace "FW bandwidth" with --FWHM bandwidth--
Col. 18, line 30: replace "to optimized" with --to optimize--
Col. 19, line 33: replace "nutation" with --mutation--
Col. 19, line 36: replace "SNIP. was" with --SNR was--
Col. 22, line 25: replace "σis" with --σ is--
Col. 24, line 61: replace "FITS" with --HTS--
Col. 26, line 29: after "frequency", insert --with a resonance linewidth.--
Col. 26, line 38: delete "and"
Col. 26, line 40: replace "response" with --response (QR)--
Col. 26, line 41: after "band", insert --wherein the QR response of the analyte has a response linewidth and a response lineshape; the resonance linewidth being less than the response linewidth; and the lineshape of the QR response being determined from data obtained at a plurality of resonance frequencies within the frequency band--
Col. 26, line 60: replace "Claim 1" with --Claim 5--
Col. 26 & 27: cancel Claim 7
Col. 27, line 4: replace "8" with --7--
Col. 27, line 7: replace "9" with --8--
Col. 27, line 11: replace "10" with --9--
Col. 27, line 13: replace "11" with --10--
Col. 28, line 1: replace "12" with --11--
Col. 28, line 9: replace "13" with --12--

UNITED STATES PATENT AND TRADEMARK OFFICE
CERTIFICATE OF CORRECTION

PATENT NO. : 7,511,500 B2
APPLICATION NO. : 11/679378
DATED : March 31, 2009
INVENTOR(S) : Jeffrey L. Schiano et al.

It is certified that error appears in the above-identified patent and that said Letters Patent is hereby corrected as shown below:

Add the following claims, col. 28, lines 9-23 should read:
--13. An apparatus to assist detection of an analyte within a sample volume using nuclear quadrupole resonance (QR), the analyte having a QR response, the apparatus comprising:
a superconducting resonator having a resonance frequency with a resonance linewidth;
a frequency controller, operable to adjust the resonance frequency of the superconducting resonator;
an electronic module, operable to adjust a fine frequency so as to locate the QR response frequency within a frequency band;
an exciter circuit, operable to excite the sample volume;
a receiver circuit, operable to receive signals from the superconducting resonator; and the frequency control using an adaptive algorithm to search for the QR response of the analyte wherein the QR response of the analyte has a response linewidth and a response lineshape; the resonance linewidth being less than the response linewidth; and the lineshape of the QR response being determined from data obtained at a plurality of resonance frequencies within the frequency band.--
Add the following claims, col. 29, lines 1-2 should read:
--14. The apparatus of claim 13, wherein the frequency control uses the adaptive algorithm to select a frequency adjustment so as to maximize the energy of the QR response.--
Line 3-5 --15. The apparatus of claim 13, wherein the frequency control uses the adaptive algorithm to select a frequency adjustment so as to minimize a covariance of the least-squares estimates of the lineshape parameters.--
Lines 6-8 --16. The apparatus of claim 13, the QR response of the analyte having a temperature dependence, wherein the frequency controller is operable to adjust the resonance frequency through a frequency band corresponding to an expected temperature range of the analyte--
Lines 9-23 --17. An apparatus to assist detection of an analyte within a sample volume using nuclear quadrupole resonance (QR), the analyte having a QR response, the apparatus comprising:
a superconducting resonator having a resonance frequency with a resonance linewidth;
a frequency controller, operable to adjust the resonance frequency of the superconducting resonator;
an electronic module, operable to adjust a fine frequency so as to locate the QR response frequency within a frequency band wherein the QR response of the analyte has a response linewidth and a response lineshape; the resonance linewidth being less than the response linewidth; and the lineshape of the QR response being determined from data obtained at a plurality of resonance frequencies within the frequency band;

UNITED STATES PATENT AND TRADEMARK OFFICE
CERTIFICATE OF CORRECTION

PATENT NO. : 7,511,500 B2
APPLICATION NO. : 11/679378
DATED : March 31, 2009
INVENTOR(S) : Jeffrey L. Schiano et al.

It is certified that error appears in the above-identified patent and that said Letters Patent is hereby corrected as shown below:

an exciter circuit, operable to excite the sample volume;
a receiver circuit, operable to receive signals from the superconducting resonator, and
wherein the frequency controller adjusts the resonance frequency of the superconducting resonator by a modification of a dielectric environment of the superconducting resonator.--
Add the following claims, col. 29, lines 24-26 should read:
--18. The apparatus of claim 17, wherein the modification of the dielectric environment of the superconducting resonator comprises an adjustment of a relative position of the superconducting resonator and a dielectric wafer.--

Signed and Sealed this

Eleventh Day of August, 2009

David J. Kappos
*Director of the United States Patent and Trademark Office*